(12) United States Patent
Claggett

(10) Patent No.: US 12,161,416 B2
(45) Date of Patent: Dec. 10, 2024

(54) DEVICES, SYSTEMS, AND METHODS FOR FUNDUS IMAGING AND ASSOCIATED IMAGE PROCESSING

(71) Applicant: Envision Ophthalmology Inc., Seattle, WA (US)

(72) Inventor: Shane Claggett, Seattle, WA (US)

(73) Assignee: Envision Ophthalmology Inc., Seattle, WA (US)

( * ) Notice: Subject to any disclaimer, the term of this patent is extended or adjusted under 35 U.S.C. 154(b) by 707 days.

(21) Appl. No.: 17/169,310

(22) Filed: Feb. 5, 2021

(65) Prior Publication Data
US 2021/0244274 A1    Aug. 12, 2021

Related U.S. Application Data

(60) Provisional application No. 62/971,872, filed on Feb. 7, 2020.

(51) Int. Cl.
*A61B 3/12*  (2006.01)
*A61B 3/00*  (2006.01)
(Continued)

(52) U.S. Cl.
CPC .............. *A61B 3/12* (2013.01); *A61B 3/0025* (2013.01); *A61B 3/0058* (2013.01); *A61B 3/08* (2013.01); *G06N 20/00* (2019.01)

(58) Field of Classification Search
CPC ....... A61B 3/12; A61B 3/0025; A61B 3/0058; A61B 3/08; G06N 20/00; G06N 3/045; G06N 3/044; G06N 3/08
See application file for complete search history.

(56) References Cited

U.S. PATENT DOCUMENTS 11,504,000 B2 * 11/2022 Khan ................. A61B 3/12
2012/0200690 A1 * 8/2012 Beasley ............. A61B 3/1208
                                                            348/78
(Continued)

FOREIGN PATENT DOCUMENTS

WO    WO-2016001868 A1 *  1/2016  ........... A61B 3/0025

OTHER PUBLICATIONS

Estrada et al ('Enhanced Video indirect ophthalmoscopy (VIO) via robust mosaicing', Biomedical Optical Express, Sep. 29, 2011, Retrieved Mar. 3, 2024(Year: 2011).*

(Continued)

*Primary Examiner* — Joseph P Martinez
*Assistant Examiner* — Ray Alexander Dean
(74) *Attorney, Agent, or Firm* — Perkins Coie LLP

(57) ABSTRACT

Introduced here are techniques to accurately and efficiently generate an image indicative of a fundus. An imaging device engaged to an ophthalmology device, such as an indirect ophthalmoscope, may capture a series of images of a fundus. The series of images may be segmented to identify a region of interest (ROI) representing the fundus in each image. The segmented series of images may be projected onto a coordinate space to remove any distortion in each of the series of images. The projected segmented series of images may be combined into an output fundus image. As a result, the output fundus image may remove distortion and glare included in the input images. The output fundus image may be utilized in detection and diagnosis of various conditions and diseases.

19 Claims, 19 Drawing Sheets

(51) Int. Cl.
*A61B 3/08* (2006.01)
*G06N 20/00* (2019.01)

(56) References Cited

U.S. PATENT DOCUMENTS

2015/0371383 A1* 12/2015 Chabrier .............. G06T 7/0014
                                                        600/476
2018/0206720 A1*  7/2018 Wang ................... A61B 3/0083
2019/0223718 A1*  7/2019 Breitenstein .......... A61B 3/135

OTHER PUBLICATIONS

Estrada, et al., "Enhanced video indirect ophthalmoscopy (VIO) via robust mosaicing," copyright 2011 Optical Society of America, published Sep. 29, 2011, Biomedical Optics Express, vol. 2, No. 10., pp. 2871-2887.

* cited by examiner

DEVICES, SYSTEMS, AND METHODS FOR FUNDUS IMAGING AND ASSOCIATED IMAGE PROCESSING

CROSS-REFERENCE TO RELATED APPLICATION(S)

The application claims priority to and the benefit of U.S. Provisional Application No. 62/971,872, filed Feb. 7, 2020, which is incorporated herein by reference in its entirety.

TECHNICAL FIELD

The present disclosure relates generally to fundus imaging, and more specifically, to device, systems, and methods for fundus imaging and associated image processing.

BACKGROUND

The ophthalmic fundus is the interior surface of the eye, and encompasses the optic disc, macula, posterior pole, vasculature, and the retina. Examination of the fundus by a trained medical professional, such as an ophthalmologist or optometrist, is necessary to diagnose and monitor retinal and systemic diseases. To view the fundus, the medical professional typically uses an ophthalmoscope, which provides a magnified view of the fundus and allows identification of various conditions and diseases. A direct ophthalmoscope, which is a simple flashlight that provides a limited view of the fundus, is used by primary care providers who do not have access to indirect ophthalmoscopic examination. An indirect ophthalmoscope-either monocular or binocular-includes a light attached to a headband and a separate lens and is able to provide a wider and overall better view of the fundus.

As an alternative or supplement to ophthalmoscopy, physicians use fundus photography to create a digital image of the fundus that is then reviewed by medical professionals to document the state of a patient's retina in order to diagnose and/or monitor the progression of numerous eye conditions and diseases. Fundus photography requires the use of highly specialized fundus cameras that include an intricate microscope attached to a flash enabled camera. There are significant benefits in the digital records created by fundus photography because the alternative—an ophthalmoscope—means the only documentation of what a physician sees is the notes in the medical record, which are based on the physician's interpretation of their real-time observations and therefore inherently subjective. However, specialized fundus cameras are large, exceptionally expensive, have high operating costs, and require a specially-trained technician to operate. Therefore, these cameras are only used on a small number of patients and are inaccessible for a large subset of operators. Thus, while it may be preferable to capture fundus images for all patients, it is unrealistic given the expense of current technologies and personnel requirements. There is a need for an accessible and efficient wide-field fundus imaging system to improve patient care, medical documentation, clinical outcomes, and education, and to provide access to ophthalmic care via telemedicine.

BRIEF DESCRIPTION OF THE DRAWINGS

The present embodiments are illustrated by way of example and are not intended to be limited by the figures of the accompanying drawings.

Like reference numerals refer to corresponding parts throughout the figures and specification.

DETAILED DESCRIPTION

Figure 1A:
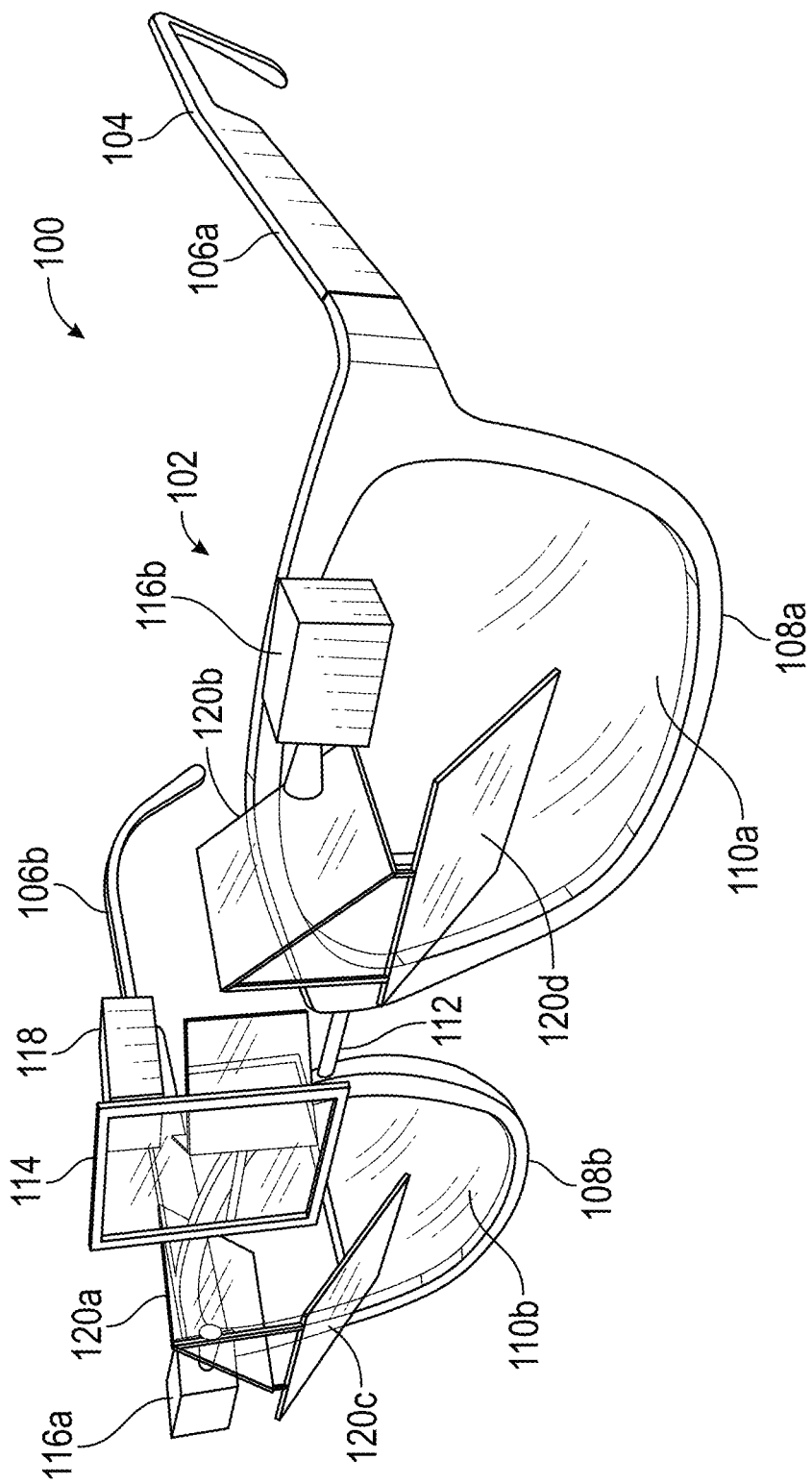
FIG. 1A is a perspective view of an indirect ophthalmoscope with an integrated imaging device configured in accordance with embodiments of the present technology.

The present technology is generally directed to devices, systems, and methods for fundus imaging and associated image processing. Specific details of several embodiments of the present technology are described herein with reference to FIGS. 1A-12. Although many of the embodiments are described with respect to devices, systems, and methods for imaging the retina, other applications and other embodiments in addition to those described herein are within the scope of the present technology. For example, at least some embodiments of the present technology may be useful for imaging other portions of the ophthalmic fundus, such as the optic disc, macula, fovea, and posterior pole, and/or other portions of the eye. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the term "fundus" generally refers to an interior surface of the eye opposite the lens and can include any of a retina, optic disc, macula, fovea, and posterior pole.

Various embodiments of the present fundus imaging technology include devices and techniques to accurately, efficiently, and more cost-effectively generate an image indicative of a fundus. For example, an imaging device may be integrated with or attached to an ophthalmology device, such as an indirect ophthalmoscope, and used to capture a series of images of a fundus without obstructing the view of the indirect ophthalmoscope operator.

The series of images obtained by the imaging device can be processed to generate an output image that represents a fundus. Particularly, the output image can include an image depicting a fundus without distortions or imperfections, such as glare.

The series of images may be segmented to identify a region of interest (ROI) representing the fundus in each image. The segmented series of images may be projected onto a coordinate space to remove any distortion in each of the series of images and compensate for any movement of the fundus between frames. The projected segmented series of images may be combined into an output fundus image. In some instances, features of each of the projected regions of interest from the images may overlap on the coordinate space. Overlapping features in one or more images projected onto the coordinate space can be combined in the output image to generate a super-resolution representation of the fundus.

As a result, the output image(s) of the fundus may remove distortion/glare in input images. Further, images that inadequately depict the fundus (e.g., an image that is out of focus, an image that failed to capture the fundus) may be rejected and not utilized in the generation of the fundus photograph. This may result in a high-resolution image of the fundus with reduced glare and distortion. The improved resultant image of the fundus may be utilized in detection and diagnosis of various ophthalmic conditions or diseases. Recent advances in medicine have also identified the potential for detection of various non-ophthalmic conditions and diseases by inspecting a fundus, such as cardiovascular and nervous system conditions. For example, fundus imaging allows for the direct observation of microcirculation of the eye, which is a direct indicator of the patient's cardiovascular health. Further, fundus imaging allows for the inspection of neurological tissue via the fundus, which is expected to be useful in detecting and monitoring neurodegenerative disorders, such as Alzheimer's disease.

Selected Embodiments of Fundus Imaging Devices

As described above, ophthalmic devices are generally used to facilitate observation of one's fundus. One such device is an indirect ophthalmoscope that allows an operator (e.g., a medical professional, ophthalmologist, optometrist) to directly view one's fundus. Ophthalmic devices can include various components that facilitate the capture of images of a fundus while limiting obstruction of a view of an operator.

Figure 1B:
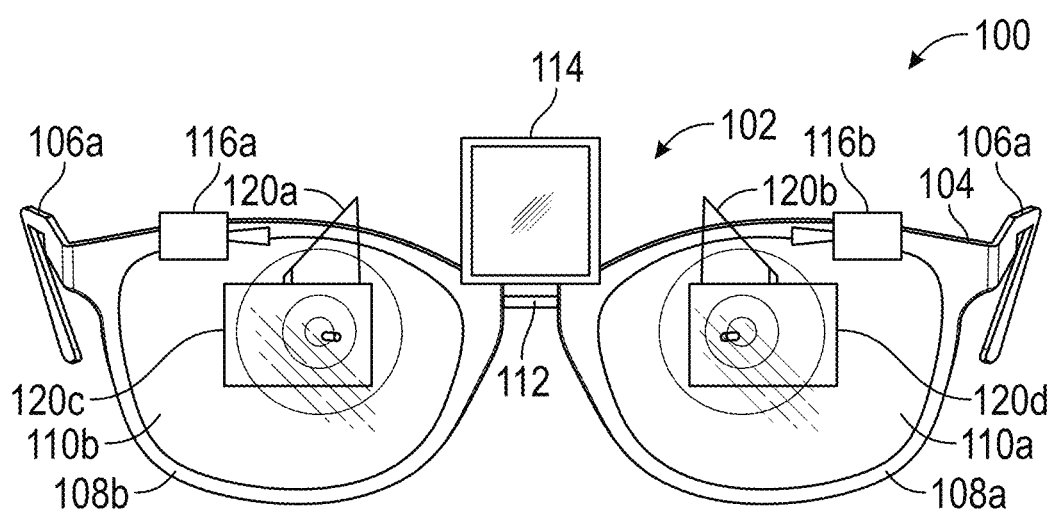
FIG. 1B is a front view of the indirect ophthalmoscope of FIG. 1A with an integrated imaging device configured in accordance with embodiments of the present technology.

FIGS. 1A and 1B are perspective and front views, respectively, of an indirect ophthalmoscope 100 with an integrated imaging device 102 configured in accordance with embodiments of the present technology. The imaging system is able to capture fundus images in real time while the operator is performing a routine fundus examination with the indirect ophthalmoscope without interfering with the operator's view or examination.

As shown in FIGS. 1A and 1B, the indirect ophthalmoscope 100 can include a frame 104 that provides a mechanism for positioning the indirect ophthalmoscope 100 appropriately in front of the user's eyes and houses or carries components of the indirect ophthalmoscope 100, including the integrated imaging device 102. In the illustrated embodiment, the frame 104 resembles a pair of reading glasses, with two temples 106a-b (also referred to as arms) that extend over the user's ears, rims 108a-b that carry lenses 110a-b, and a bridge 112 connecting the rims 108a-b. In other embodiments, the frame 104 can include a band that encircles and/or extends over an operator's head and secures to an eyepiece (e.g., similar to the headband structure used in other indirect ophthalmoscopes), and/or the frame 104 may have additional or other suitable structures for appropriately positioning the ophthalmoscope 100.

The indirect ophthalmoscope 100 can further include features of the imaging device 102, such as a viewport 114, one or more cameras (identified individually as a first camera 116a and a second camera 116b, referred to collectively as "cameras 116") for capturing fundus images, and a lamp 118 with an internal aim/focus mechanism. The viewport 114 and the lamp 118 are positioned relative to the lenses 110a-b (e.g., superior to lenses 110a-b) such that they do not interfere with the operator's normal view when the system is off and also allow for the concurrent real-time viewing of the fundus by the operator via the lenses 110a-b, while the camera(s) 116 takes a video or images of the fundus without obstructing the view of the operator. In some embodiments, the viewport 114 may incorporate polarizing filters to reduce the amount of glare reaching physician and/or the camera(s) 116. In other embodiments, lenses 110a-b may include polarizing filters to reduce glare reaching the eyes of the operator.

In the embodiment illustrated in FIGS. 1A and 1B, the indirect ophthalmoscope 100 includes two cameras 116 positioned on opposite sides of the viewport 114 generally above the user's site line (with respect to the lenses 110a-b) and directed toward the viewport 114. The cameras 116 can capture images (singular images, a stream of images, and/or videos) representative of a fundus. In some embodiments, cameras 116 can capture images of the fundus from different perspectives, and these captured images can be combined to provide a stereoscopic view of the fundus.

The indirect ophthalmoscope 100 can include a plurality of substrates 120a-d that can modify (e.g., reflect, refract, diffract, absorb) light so as to direct light and/or improve the images captured by cameras without obstructing the view of the operator. The substrates 120 can include films on or integrated with the substrates 120a-d, the view port 114, the lenses 110a-b, and/or other imaging and viewing components of the indirect ophthalmoscope 100.

The films may have adjustable opacity for various uses and effects. The opacity may be adjusted electronically via a controller (e.g., computing device 208, control circuit 210). In some embodiments, the opacity of substrates 120a-d can adjust a light path along the indirect ophthalmoscope 100. Films with an adjustable opacity (or simply "smart glass") can alter light transmission properties in response to an applied input (voltage, light, heat, etc.). In some embodiments, the films may switch between transparent and opaque in response to an applied voltage. The films may include components relating to suspended-particle devices, electrochromic devices, and/or polymer-dispersed liquid-crystal devices, for example.

In some embodiments, the substrates 120a-d can include beam splitters that split light into multiple beams that can be captured by cameras 116a-b. In other embodiments, the beam splitters can be replaced by mirrors in order to increase the amount of light reaching the physician's eyes and improve their view. This may be accomplished by offsetting the cameras 116a-b such that each camera captures a slightly different view of a fundus.

Figure 1C:
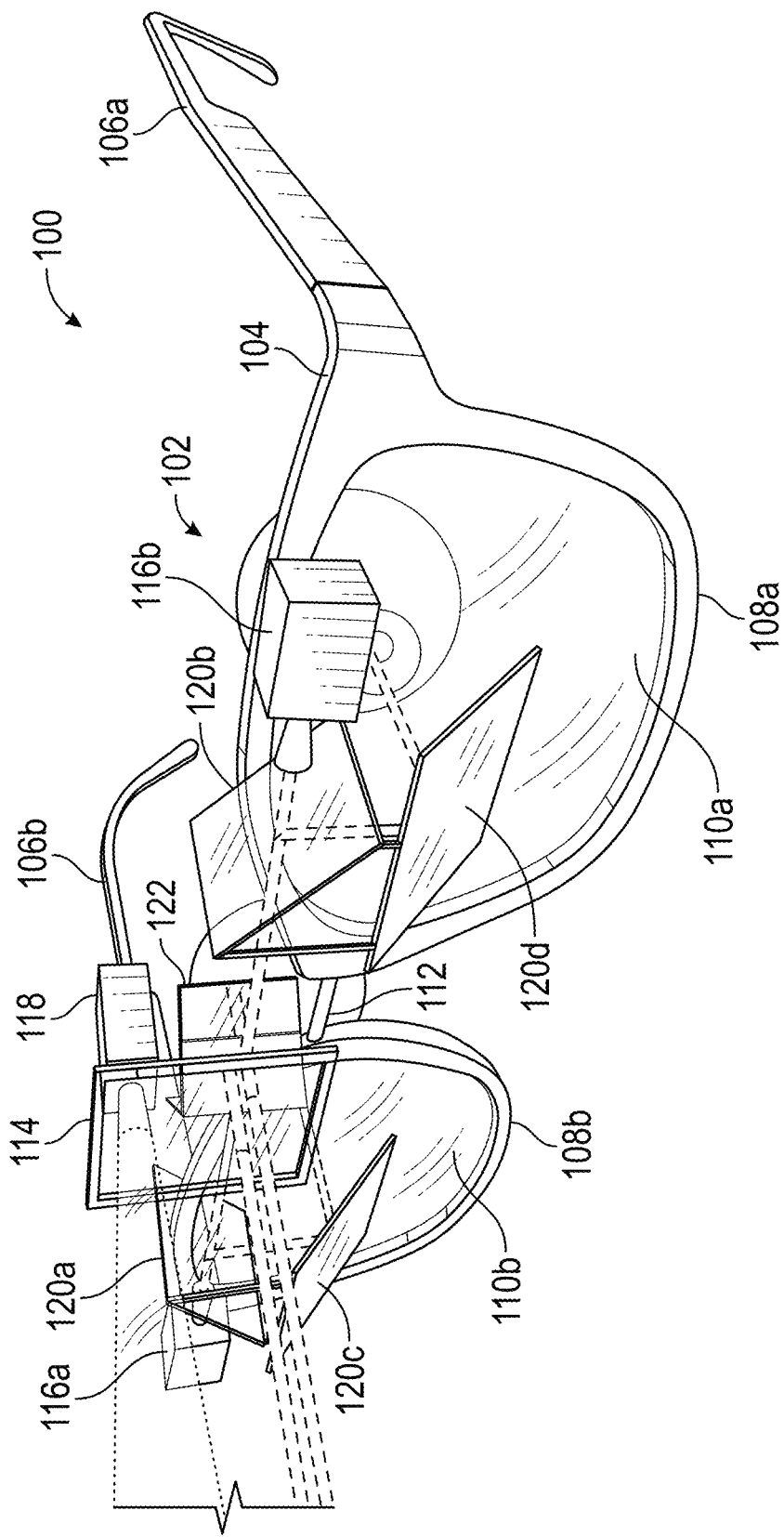
FIG. 1C is a perspective view of an indirect ophthalmoscope of FIG. 1A with an integrated imaging device configured in accordance with embodiments of the present technology.

FIG. 1C is a perspective view of an indirect ophthalmoscope 100 of FIG. 1A with an integrated imaging device 102 configured in accordance with embodiments of the present technology. As shown in FIG. 1C, the indirect ophthalmoscope 100 and integrated imaging device 102 may facilitate modification of light paths along the indirect ophthalmoscope 100. For example, in FIG. 1C, an operator's central vision may be replaced by an indirect view through viewport 114. Particularly, substrates 120a-d may reflect light along a light path to mirrors 122. The mirrors 122 can redirect the light through viewport, allowing for an indirect view of a fundus.

Figure 1D:
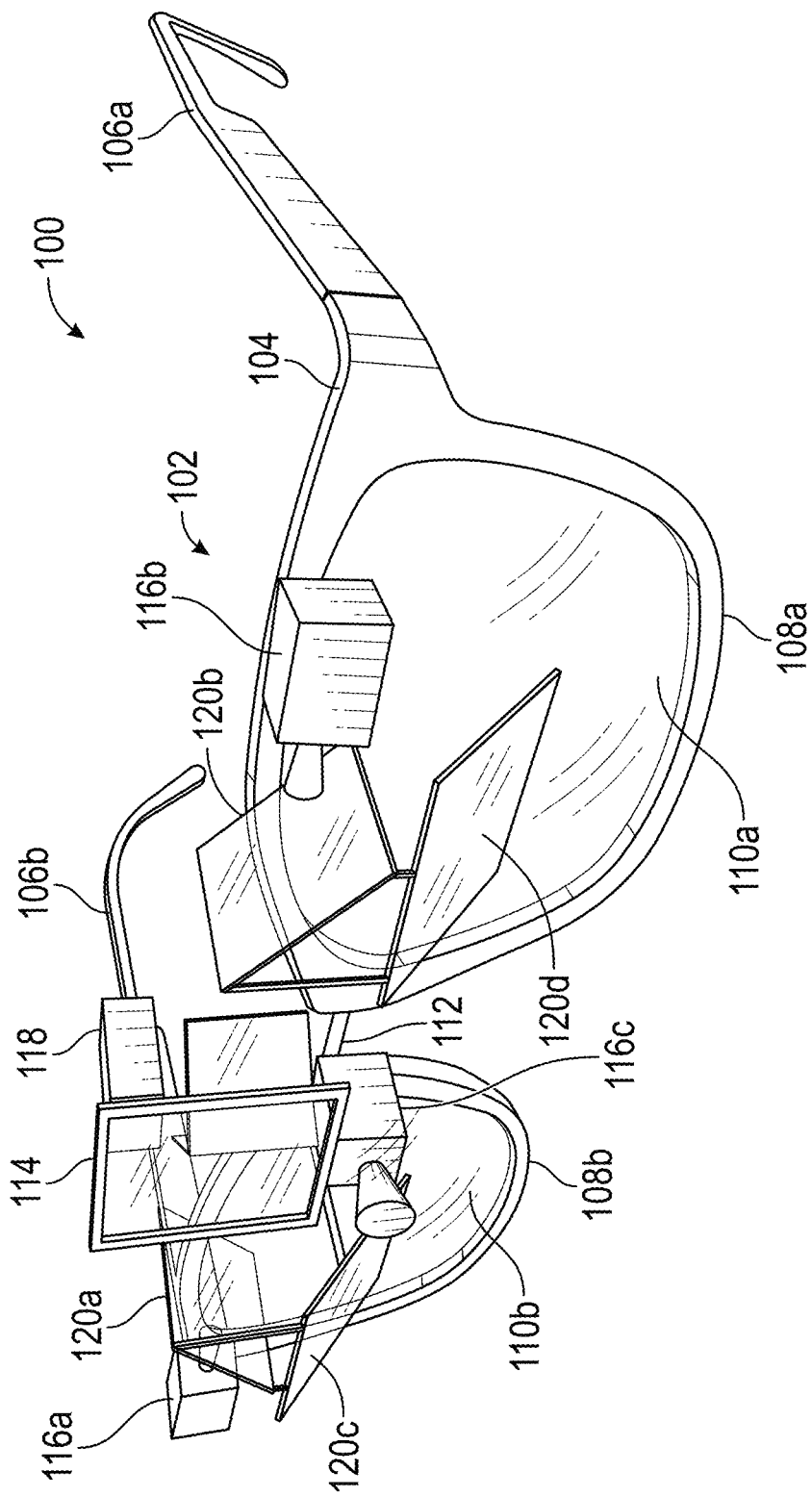
FIG. 1D is a perspective view of an indirect ophthalmoscope with an integrated imaging device including three cameras configured in accordance with embodiments of the present technology.

FIG. 1D is a perspective view of an indirect ophthalmoscope 100 with an integrated imaging device 102 including three cameras 116a-c configured in accordance with embodiments of the present technology. In the embodiment as shown in FIG. 1D, the indirect ophthalmoscope 100 can include three cameras 116a-c. Particularly, two cameras 116a-b can be positioned opposing to one another and directed at one another, while a third camera 116c can be positioned between cameras 116a-b and directed at a direction perpendicular to that of cameras 116a-b.

The third camera 116c can include a low-resolution, wide-angled camera that can be used to detect when the indirect ophthalmoscope 100 is directed at the fundus. This can include periodically capturing an image and inspecting the image to determine whether a fundus is depicted in the image. Based on determining that a fundus is depicted in the image, two high-resolution cameras 116a-b can be aimed and focused to capture images of the fundus.

Figure 1E:
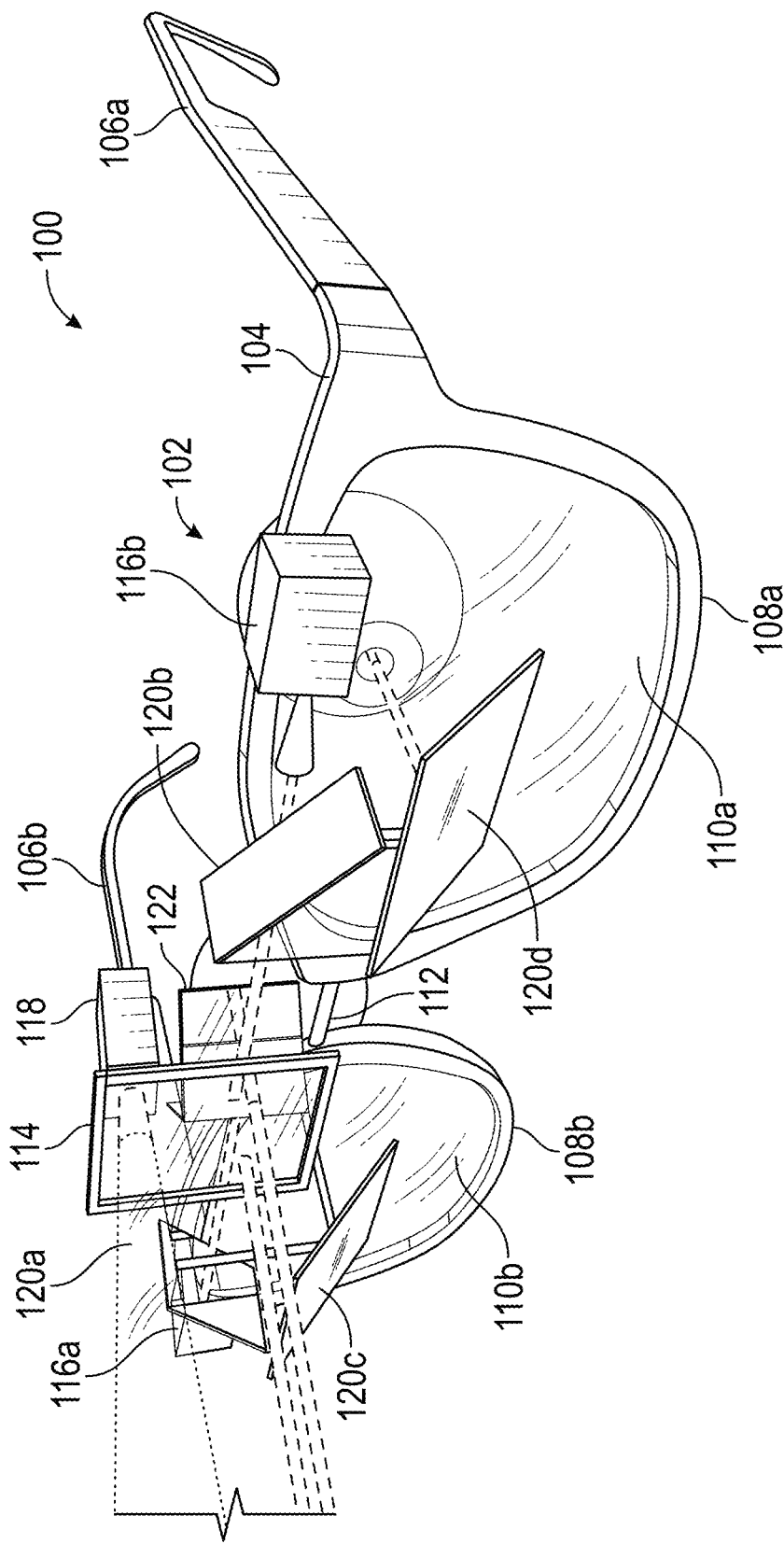
FIG. 1E is a perspective view of an indirect ophthalmoscope with an integrated imaging device configured in accordance with embodiments of the present technology.

FIG. 1E is a perspective view of an indirect ophthalmoscope 100 with an integrated imaging device 102 configured in accordance with embodiments of the present technology. As shown in FIG. 1E, the substrates 120a-b can include mirrors that can modify the light path and improve the operator's view of the fundus through viewport 114. In some embodiments, the cameras 116a-b may be positioned offset slightly to obtain a field of view through viewport 114 directly via mirrors 122 without passing through substrates 120a-b.

In some embodiments, the light path of the indirect ophthalmoscope 100 may be electrically controlled, e.g., by using the films adjacent to or disposed on substrates 120a-d or mirrors 122, depending upon the specific use of the device. For example, the indirect ophthalmoscope 100 may have a first state (also referred to as an "off state"). In the first state, the cameras 116a-b and lamp 118 can be turned off, the films on the substrates 120c-d in front of the user's eyes are transparent, and the film in the viewport 114 is opaque. This configuration disables the indirect view and allows to user to see straight ahead through the lenses 110a-b.

The indirect ophthalmoscope 100 may have a second state (also referred to as an "on state") that provides the indirect viewing. In the second state, the cameras and lamp can be turned on, the films on the substrates 120c-d in front of the lenses 110a-b are opaque, and the film in the viewport is transparent. This configuration disables the direct view (i.e., straight forward) via the lenses, so the physician's central vision is replaced by the indirect view.

Figure 1F:
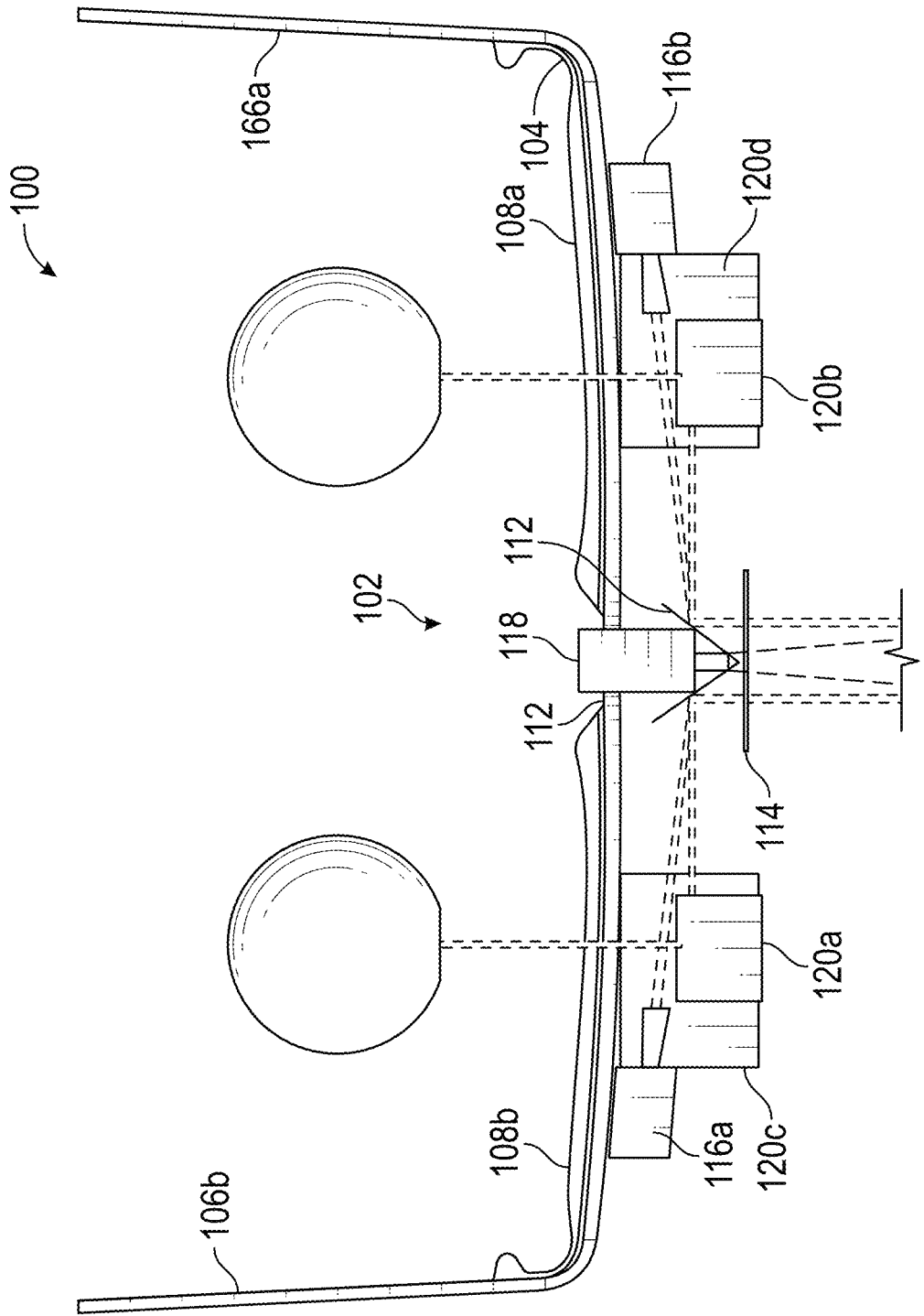
FIG. 1F is a top view of an indirect ophthalmoscope with an integrated imaging device configured in accordance with embodiments of the present technology.

FIG. 1F is a top view of an indirect ophthalmoscope 100 with an integrated imaging device 102 configured in accordance with embodiments of the present technology. As shown in FIG. 1F, a light path of an operator may be redirected via substrates 120a-d. As noted above, substrates 120a-b can include mirrors to redirect light along the light path. The light path of both the operator and the cameras 116a-b may be reflected using mirrors 122 through the viewport 114.

In some embodiments, the indirect ophthalmoscope 100 can include features customized for one or more specific users. For example, the lenses 110a-b may include the user's prescription to avoid the user needing to wear glasses or contacts behind the indirect ophthalmoscope 100. The indirect ophthalmoscope can also or alternatively be customized or adjusted (e.g., via an internal mechanism) to correspond to the user's interocular distance and the proper aim/focus.

Figure 2A:
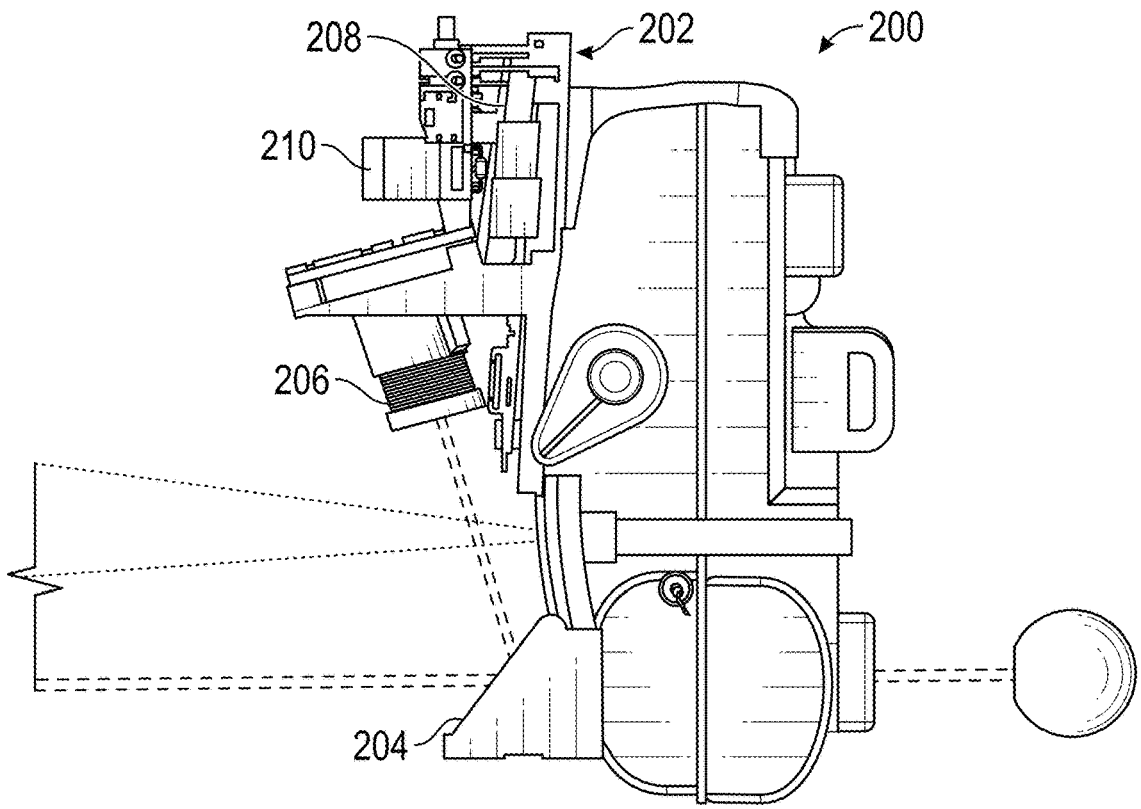
FIG. 2A is a side view of an indirect ophthalmoscope with an attached imaging device configured in accordance with embodiments of the present technology.
Figure 2B:
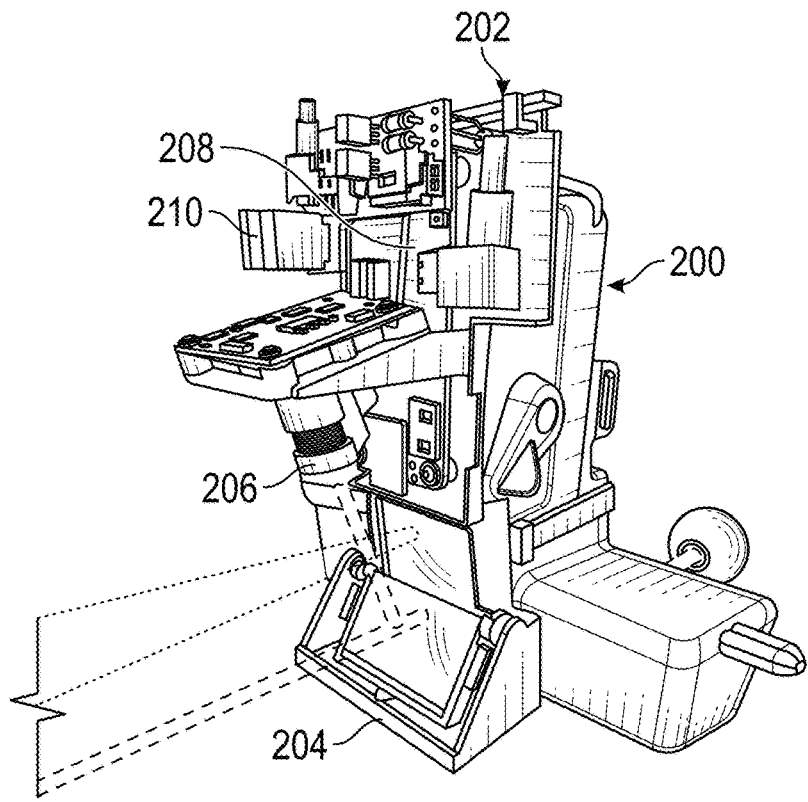
FIG. 2B is a perspective view of the indirect ophthalmoscope with the attached imaging device of FIG. 2A.

FIGS. 2A and 2B illustrate a side view and a perspective view, respectively, of an indirect ophthalmoscope 200 with an attached imaging device 202 configured in accordance with embodiments of the present technology. The imaging device 202 may position a beam splitter 204 disposed below a camera 206 such that the beam splitter 204 can split a beam of light between both the camera 206 and the eyes of the operator. In some cases, beam splitter 204 can be a mirror (e.g., a semi-silver mirror) that is disposed in front of an indirect view port. The angle of a mirror may be adjusted via multiple fasteners (e.g., set screws) in the imaging device 202.

The imaging device 202 can include an imaging sensor 206 (e.g., camera) mounted such that the imaging sensor 206 is aimed at the beam splitter 204. The positioning of the imaging sensor 206 and the beam splitter 204 may allow for capture of fundus images without obstructing manual observation of the fundus. For example, the beam splitter 204 can provide an image of the fundus to both the camera 206 and the eyes of the observer by splitting light between the camera 206 and the eyes of the observer.

The imaging device may include a computing device 208 (a microprocessor, embedded computer, etc.) that is in electrical communication with the imaging sensor 206. The computing device 208 may instruct the imaging sensor 206 to capture images and receive the captured images from imaging sensor 206. The computing device 208 may perform processing tasks with respect to any of the images and/or send image data to an external computing device capable of performing such processing tasks. The imaging device 202 may include one or more status indicators (e.g., light emitting diode(s), display) indicating a state/status of the imaging device 202. The imaging device 202 can include a control circuit 210 to facilitate control of the components as described herein.

The light path of light incoming may be intercepted by beam splitter 204 and redirected to the imaging sensor 206. The majority of the light can continue on through the indirect optics to an operator.

The arrangement of components of the imaging device 202 can utilize less light than other imaging devices such that a greater amount of light is directed to the eyes of the operator. For instance, the arrangements of substrates (e.g., substrates 120a-d in FIGS. 1A-1F) and mirrors may direct light to both the camera 206 and to the operator. This may increase the utilization of an indirect ophthalmoscope by an operator. This percentage of light directed to the camera 206 may be reduced even lower if it is found to still acquire a usable video.

The imaging device 202 may transmit video frames to the imaging server in real time or near-real time, while other devices may record the video frames to a video file on a memory card to be processed at a later time.

In some embodiments, imaging device 202 may include an auto-focusing mechanism. The auto-focusing mechanism can dynamically adjust a zoom of the camera 206 so as to maintain a focus onto the fundus by camera 206.

In various embodiments, the imaging device 202 can include one or more status indicators that provide sensory indications (e.g., visual, audio, tactile) of various states of the system to the user. For example, the imaging device 202 can include one or more LEDs that use various colors to indicate the state of the software. For example, if the LED is off, the instructions are not executing on the computing device. As another example, if the LED is green, the system is ready to capture images and/or process images. If the LED is flashing green, the camera may be capturing images. If the LED is flashing red and green, the system may have encountered an error (e.g. unable to reach imaging server). If the LED is solid red, the system may have encountered a fatal error (e.g. hardware failure).

Figure 3A:
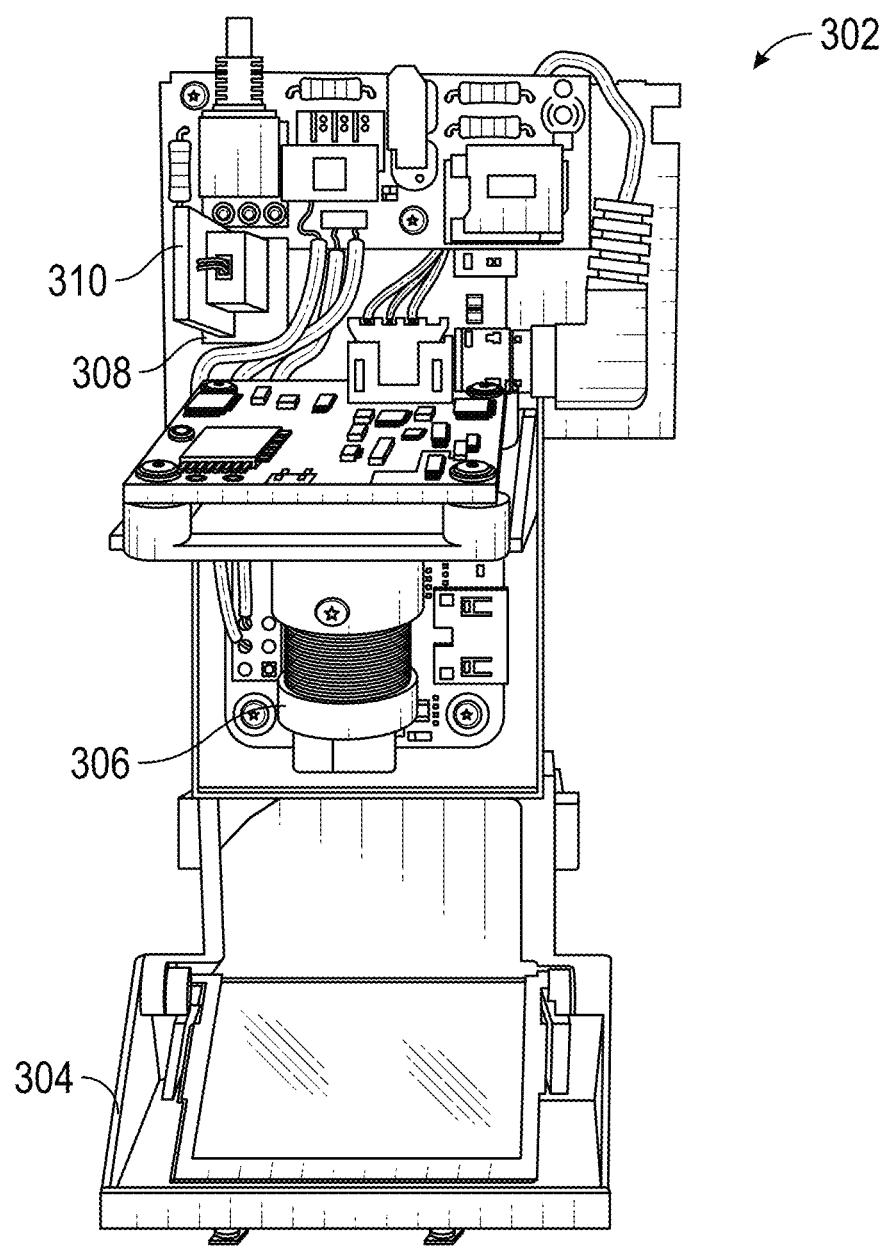
FIG. 3A is a front view of an imaging device for attachment to an ophthalmoscope in accordance with embodiments of the present technology.
Figure 3B:
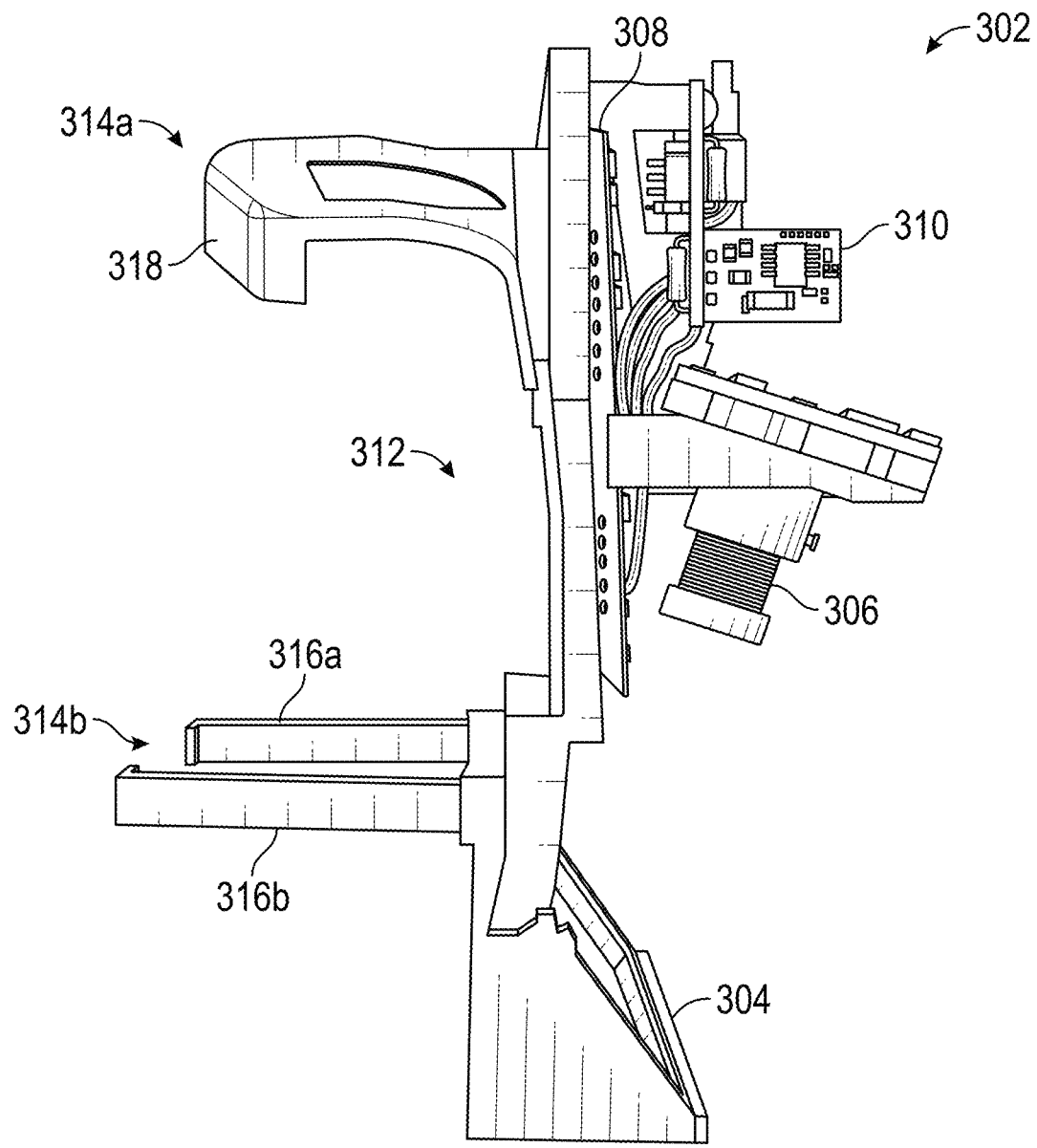
FIG. 3B is a side view of an imaging device of FIG. 3A configured in accordance with embodiments of the present technology.
Figure 3C:
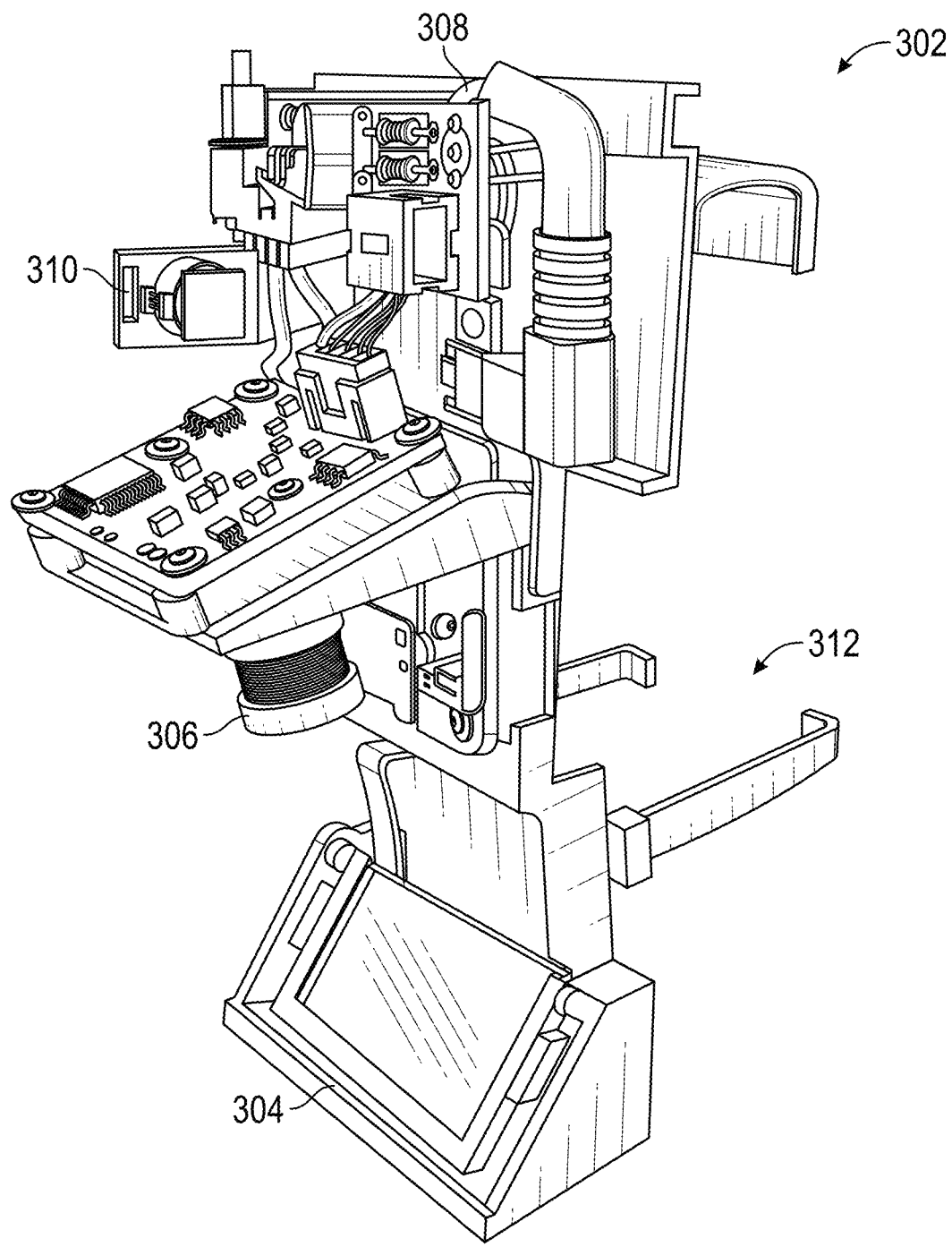
FIG. 3C is a perspective view of an imaging device of FIG. 3A configured in accordance with embodiments of the present technology.

FIGS. 3A-3C illustrate a front view, a side view, and a perspective view, respectfully, of an imaging device 302 configured in accordance with embodiments of the present technology. The imaging device 302 can be removably attached to an indirect ophthalmoscope (e.g., the ophthalmoscope 200 of FIGS. 2A and 2B) or other ophthalmic visualization device via a connector assembly 312. The imaging device 302 can include any of a beam splitter 304, a camera 306, a computing device 308, and a control circuit 310. The imaging device 302 as described in FIGS. 3A-3C may include components and features similar to the attached imaging device 202 as described with respect to FIGS. 2A-2B.

The connector assembly 312 can include a plurality of mechanisms for releasably or permanently attaching the imaging device 302 to an ophthalmic visualization device. In the embodiment illustrated in FIGS. 3A-3C, for example, the connector assembly 312 includes a first attachment portion 314a configured to grasp or otherwise connect to a first portion of the ophthalmic visualization device and a second attachment portion 314b configured to grasp or otherwise connect to a second portion of the ophthalmic visualization device. The second attachment portion 314b may include two brackets 316a-b that clamp onto the second portion of the ophthalmic visualization device, and the first attachment portion 314b may be an engagement arm 318 that extends at least partially around the first portion of the ophthalmic visualization device. In these and other embodiments, the attachment portions 314a-b can include other or additional coupling mechanisms that provide for releasable or permanent engagement to an indirect ophthalmoscope or other ophthalmic visualization device, such as retractable arms, interfacing surfaces, snaps, adhesives (e.g., Velcro, glue), and screws. In some embodiments, the connector assembly may only include one connector portion or may include more than two connector portions.

Selected Embodiments of Image Processing

As noted above, images of a fundus can be acquired by an imaging device (e.g., imaging device 202) and provided to a computing device. Upon acquisition of one or more images, the acquired images may be processed to derive high-accuracy output images. As described herein, the output images may be representative of a fundus, but the present embodiments can be configured to derive output images depicting any suitable object/feature.

Figure 4:
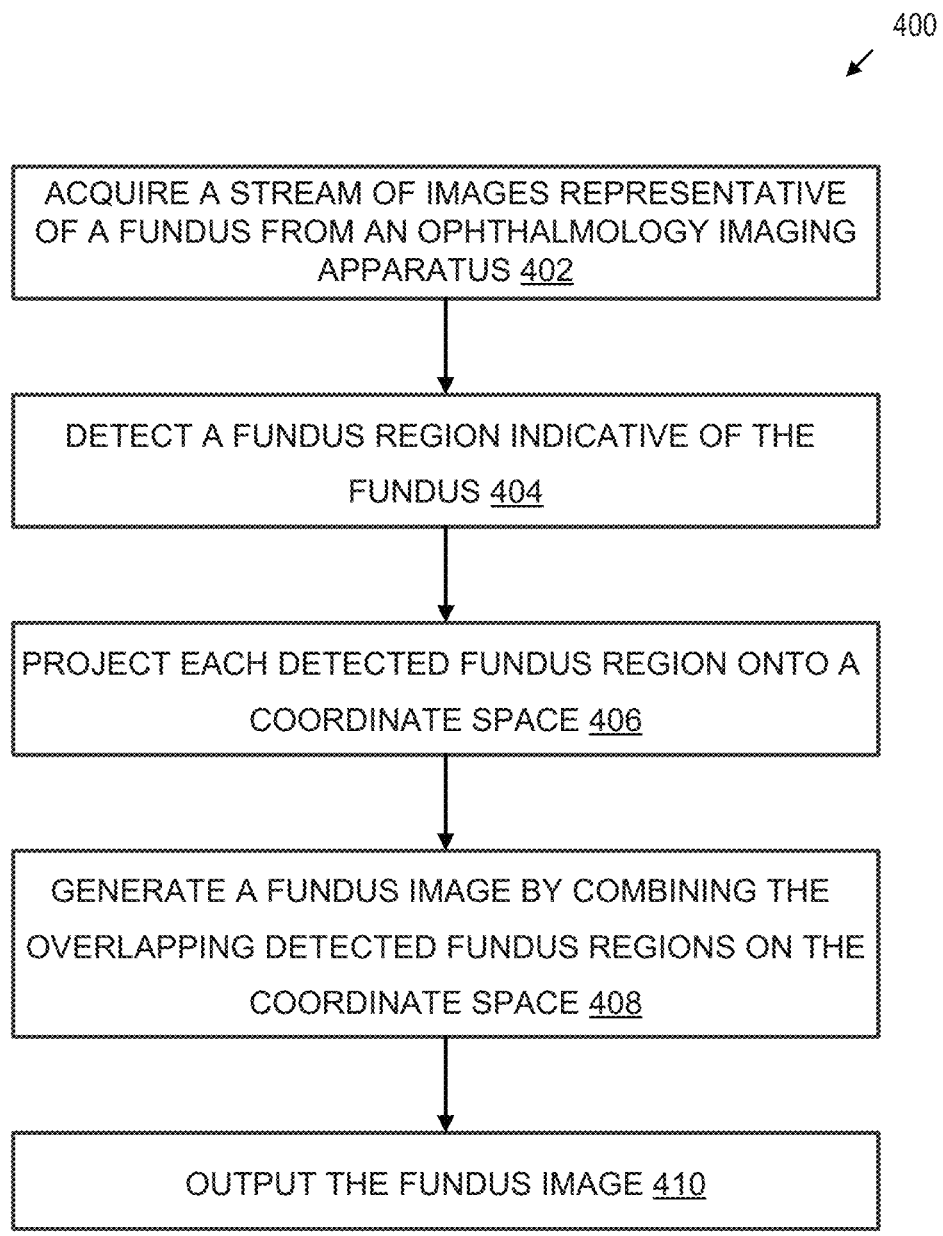
FIG. 4 is a flow process for processing input images to derive an output in accordance with embodiments of the present technology.

FIG. 4 is a flow process 400 for processing input images to derive an output in accordance with embodiments of the present technology. The method may include acquiring a stream of images representative of a fundus from an ophthalmology imaging apparatus (block 402). The input images may include any of a two-dimensional (or "2D") or three-dimensional (or "3D") image or model. In some embodiments, the input images may be acquired via an imaging device. The input images may include a series of images of a fundus captured as part of an image stream. However, many images captured may not capture the fundus or may include imperfections, such as glare or distortion.

In some embodiments, two imaging sensors included on the indirect ophthalmoscope can obtain multiple images indicative of the fundus from varying perspectives. These multiple images obtained by the two imaging sensors can be combined to generate a stereoscopic image indicative of the fundus, each stereoscopic image included as one of the images included in the stream of images. The stereoscopic image can be processed as described herein to provide an accurate depiction of a fundus.

In some embodiments, the indirect ophthalmoscope can include three cameras. A first image sensor can include a wide-angle image sensor that can capture an initialization image. The initialization image can be inspected to determine whether the initialization image depicts the fundus. If the initialization image does not depict a fundus, subsequent initialization images can be captured and inspected to determine whether the image depicts a fundus. Responsive to determining that the initialization image depicts the fundus, the two imaging sensors disposed adjacent to the wide-angle image sensor on the indirect ophthalmoscope can capture multiple images indicative of the fundus from varying perspectives. This can increase efficiency in computational resources, as only images that depict a fundus need to be processed to generate an output image of the fundus.

The method may include, for each acquired image in the stream of images, detecting a fundus region indicative of the fundus (block 404). The fundus region can include a region of interest that is indicative of a fundus. Detecting the fundus region can remove undesired regions of an image, such as portions of an image that show an examination room, a face of the patient, or glare or distortions, for example. The region of interest may include an area of the image that depicts the fundus, for example. The segmentation step may remove portions of each image that include distortion or glare. Further, if it is determined that the fundus is not adequately shown in an image, the image may be removed from the image stream.

In some embodiments, various models can be utilized in detecting the fundus region. As an example, a model can include a convolutional neutral network that has been previously trained on a dataset of segmented images, some of which are indicative of fundus regions and others which are not, and which can produce an output specifying which portion of a novel input image is indicative of a fundus, if any. Images where one or more parameters of the segmented fundus region (e.g. size, focus, clarity) that are below threshold values can be rejected from being projected onto the coordinate space.

As another example, a model can include a recurrent neural network that has been previously trained on a dataset of sequential segmented images, some of which are indicative of fundus regions and others which are not, and which can produce an output specifying which portions of a novel sequence of input images are indicative of a fundus, if any. Images where one or more parameters of the fundus region are below threshold values can be rejected from being projected onto the coordinate space.

The method may include projecting each detected fundus region onto a coordinate space (block 406). The projection of one or more detected fundus regions onto the coordinate space may result in overlap of portions of the detected fundus regions.

The method may include generating a fundus image by combining the overlapping detected fundus regions on the coordinate space (block 408). The single output image may include a high-accuracy depiction of the region of interest. Further, in some embodiments, the output image may be a super-resolution image based on the overlapping regions of interest.

In some embodiments, generating the fundus image can include identifying positions on the coordinate space with overlapping pixels indicative of similar positions of multiple detected fundus regions on the coordinate space. The pixel characteristics of the overlapping pixels included in the identified positions on the coordinate space can be averaged to produce the output fundus image.

In some embodiments, generating the fundus image can include identifying positions on the coordinate space with overlapping pixels indicative of similar positions of multiple detected fundus regions on the coordinate space. The pixel characteristics of the overlapping pixels included in the identified positions on the coordinate space can be combined to produce an output fundus image with a higher resolution than that of any image included in the stream of images.

The method may include outputting the fundus image (block 410). Outputting the fundus image can include sending the fundus image to an identified device or displaying the fundus image on a display of an identified device. The fundus image can be inspected to identify characteristics of the fundus indicative of various conditions/diseases.

Image Acquisition: As noted above, one or more images of a fundus may be acquired using one or more imaging devices (e.g., cameras 116a-b, imaging sensor 206). The images may be captured by an imaging device on an ophthalmic device, such as an indirect ophthalmoscope.

In some embodiments, a single camera may capture a series of images in an image stream. In other embodiments, multiple cameras may be used to capture stereoscopic images that provide a wider field of view. In some instances, the device may employ multiple cameras that each capture a narrow field of view through a non-mydriatic (undilated) pupil.

The imaging device may use any of a variety of sensors (e.g. CMOS, CCD), color filters (e.g. Bayer), demosaicing algorithms, and image compression algorithms (e.g. lossy or lossless). The imaging device may include components that allow for aiming/focusing of the camera to keep the target in focus.

Figure 5:
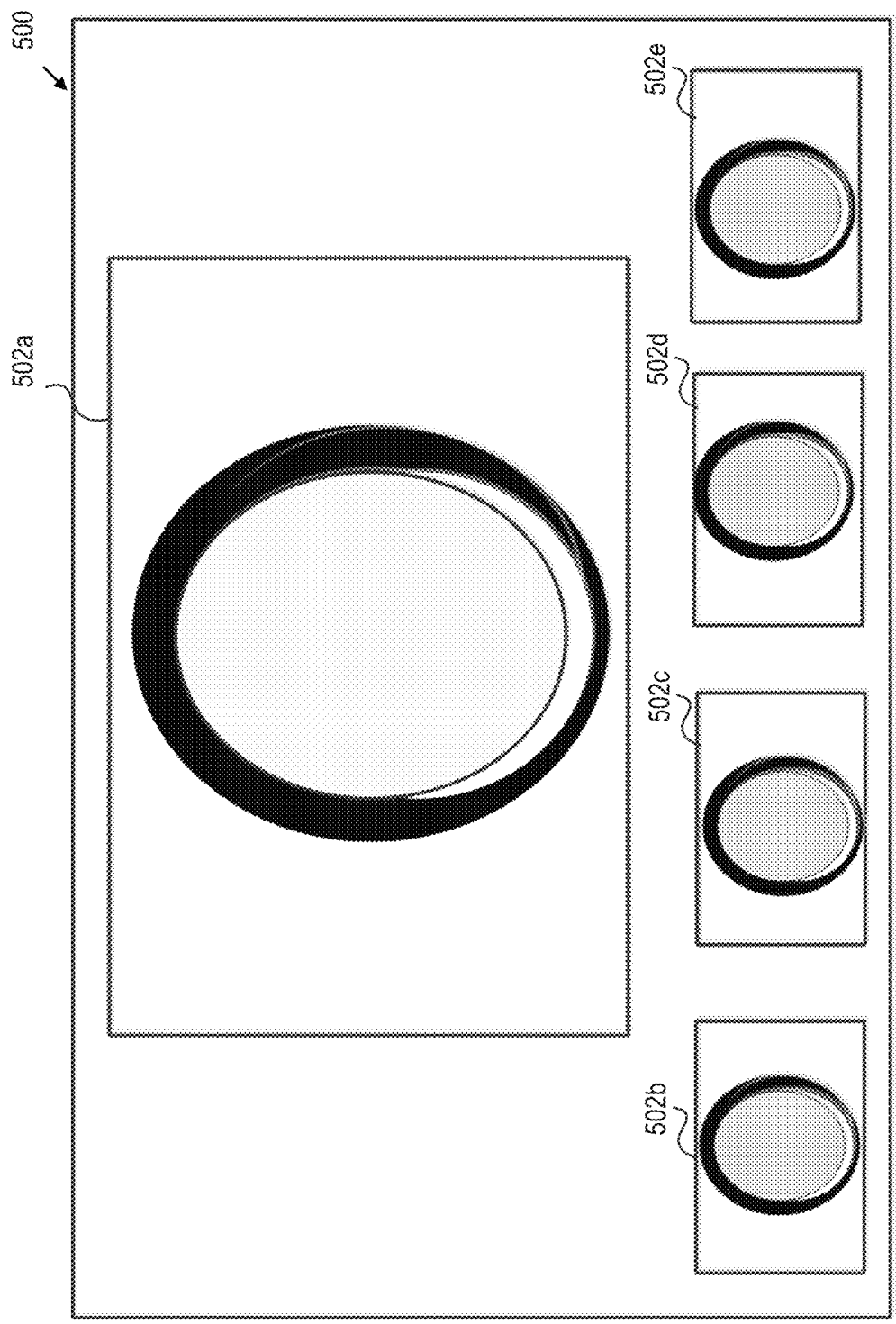
FIG. 5 is an example interface depicting a series of captured images in accordance with embodiments of the present technology.

FIG. 5 is an example interface 500 depicting a series of captured images in accordance with embodiments of the present technology. As shown in FIG. 5, a series of images 502a-e can be presented in the interface 500. The images 502a-e can be presented chronologically, as each image can be associated with a timestamp indicative of a time of capture. As described in greater detail below, the images may be inspected and processed to derive a high-accuracy output image.

Figure 6:
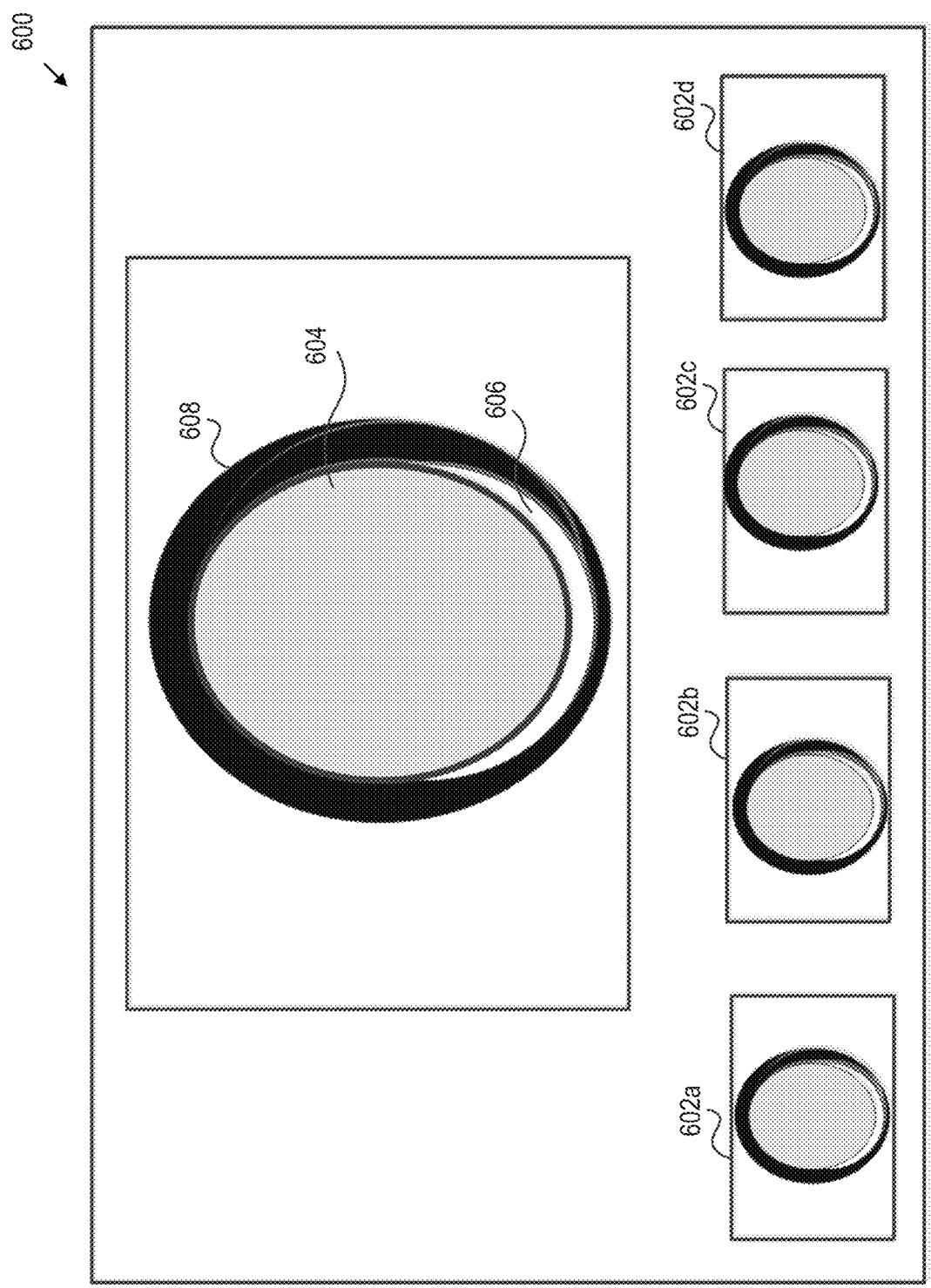
FIG. 6 is an example interface depicting a segmented image.

Image Segmentation: Segmentation of an image can include processing the image to identify a region of interest. A region of interest can include a portion of an image that identifies a target object, such as a fundus or retina. FIG. 6 is an example interface 600 depicting a segmented image.

As shown in FIG. 6, an image 602a-d may include a region of interest 604 that includes an area depicting the fundus. Further, the image 602a-d may include discarded areas 606, 608. Discarded areas 606, 608 may include regions of the image 602a-d that do not adequately depict the target object or is an area with glare, distortion, etc. For example, a first discarded area 606 can include a region with glare, and a second discarded area 608 can include an area that does not include the fundus. The discarded areas 606, 608 can be removed from the image so that the segmented image only includes the region of interest 604.

Various models can be utilized to increase the accuracy in determining the region of interest of an image. Example models can include a convolutional neutral network (CNN) or a recurrent neural network (RNN). These models can receive an input and generate an output (e.g., a predicted output) based on the received input. Some models can include parametric models that can generate the output based on the received input and on values of the parameters of the model.

In some instances, the models can include deep models that employ multiple layers of models that can generate an output for a received input. For example, a deep neural network includes a deep machine learning model that includes an output layer and one or more hidden layers, each applying a non-linear transformation to a received input to generate an output.

The model utilized in processing input images may include a convolutional neural network. A convolutional neural network can include a set of convolutional neural network layers, which may be followed by a set of fully connected layers, and an output layer. In operation, a deep convolutional neural network may include other types of neural network layers (e.g., pooling layers, normalization layers, etc.) and may be arranged in various configurations (e.g., as multiple modules, multiple subnetworks, etc.).

The model utilized in processing input images may include a recurrent neural network. A recurrent neural network can include a neural network that receives an input sequence and generates an output sequence from the input sequence. Particularly, a recurrent neural network can use some or all of an internal state of the network after processing a previous input in the input sequence in generating an output from the current input in the input sequence.

In some embodiments, multiple independent models can be utilized in parallel to combine outputs to generate an accurate result. Each independent machine learning model can generate a similar type of model output, and the model outputs can be combined and treated as the model output.

In some embodiments, prior to processing the fundus image data using one or more models, the system can pre-process the fundus images. For instance, for a given image, the system can apply any of a variety of image processing techniques to the image to improve the quality of the output generated by the machine learning model. As an example, the system may crop, scale, deskew, or re-center the image. As another example, the system can remove distortion from the image (e.g., to remove blurring or to re-focus the image), using various image processing techniques.

In implementations where the fundus image data includes a single fundus image for each point in time, the model may be a feedforward machine learning model that has been configured by being trained on appropriately labeled training data to process the fundus image data and to generate a model output that identifies the portion of the image indicative of a fundus. For example, the fundus image processing machine learning model may be a deep convolutional neural network.

In implementations where the fundus image data includes multiple fundus images for each point in time where each depicts the patient's fundus from a different perspective, the fundus image processing machine learning model may be a feedforward fundus image processing machine learning model that has been configured by being trained on appropriately labeled training data to process all perspectives from each time point simultaneously to generate a model output that identifies the portion of each image that is indicative of a fundus. For example, the fundus image processing machine learning model may be a deep convolutional neural network that includes multiple towers of convolutional layers.

In implementations where the fundus image data includes a temporal sequence of fundus images, the fundus image processing machine learning model may be a recurrent fundus image processing machine learning model that has been configured to process each image in the temporal sequence one by one to, for each image, update the internal state of the recurrent fundus image processing machine learning model, and to, after a certain number of images in the temporal sequence have been processed, start generating model outputs that identifies the portion of the images indicative of a fundus. For example, the fundus image processing machine learning model may be a recurrent neural network that includes one or more long short-term memory (LSTM) layers.

Figure 7:
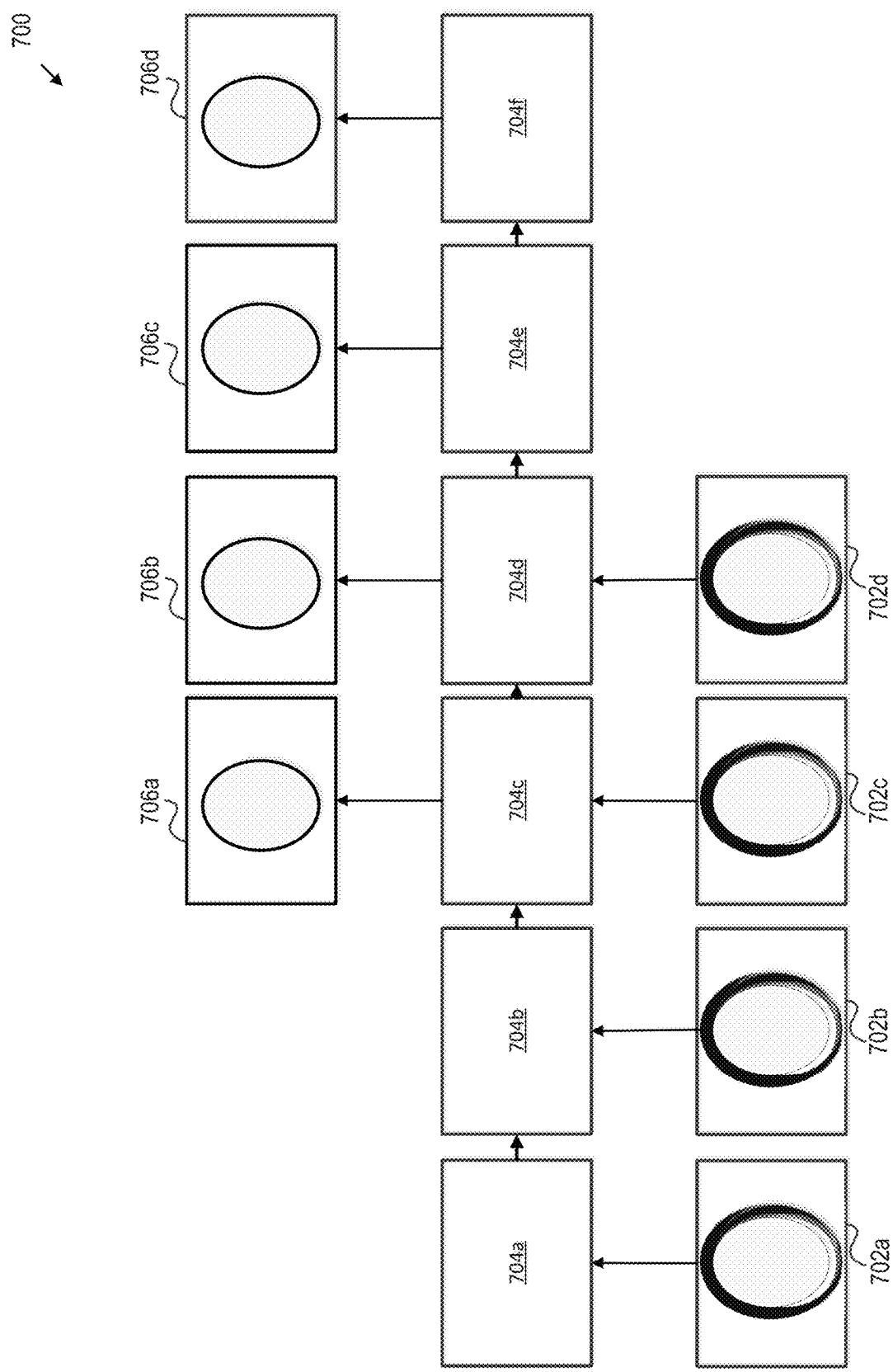
FIG. 7 is a block diagram illustrating segmentation of an image in the context of other images that occur near that point in time in accordance with embodiments of the present technology.

In some embodiments, the region of interest for an image can be detected in relation to other images with respect to time. FIG. 7 is a block diagram 700 illustrating segmentation of an image with respect similar images with respect to time in accordance with embodiments of the present technology.

As shown in FIG. 7, a stream of images 702*a-d* can be arranged with respect to time. For instance, images 702*a-d* can be associated with a timestamp. For example, a first image 702*a* can be associated with the first timestamp.

This temporal sequence of images may be fed into a fundus image processing machine learning model that is a recurrent neural network. The images may be fed in one by one to, for each image, update the internal state of the model. The state at each point in time is based on both the current input image and the model's previous state. For example, the internal state 704*b* is based on the input image 702*b* and the internal state 704*a* from the previous step.

After a certain number of images in the temporal sequence have been processed, the model may start generating outputs that identifies the portion of the input images that is indicative of a fundus. These segmented output images may also be arrange with respect to time, in the same order as the input images but delayed by a number of steps. For example, the output image 706*b* may correspond to the same timestamp at the input image 702*b* and may contain the region of the input image that is indicative of a fundus.

Segmenting images in the context of a temporal sequence using e.g. a recurrent neural network model may produce a greater accuracy of fundus region detection than a model that segments each image independently e.g. a convolutional neural network.

In some embodiments, input information can be modified based on obtained feedback data. Feedback data can include information relating to an accuracy of a detected region of interest in an image. For example, an accuracy of a detected region of interest in an image can include a value that is reduced if a portion of the fundus is not included in the detected region of interest. Conversely, this value can be increased based on the fundus being included in the region of interest. The feedback data can include annotations provided in ground-truth images of a fundus. For example, images from a fundus camera or an image of a dissected retina can be included in the input information.

The feedback data can be based on an indication from an operator providing an accuracy of the detected region of interest. The feedback data can also be based on a calculated accuracy of the detected region of interest. For example, a detected region of interest can be compared with a previously-verified region of interest to generate an accuracy rating. The accuracy rating can indicate a confidence in the detected region of interest. The accuracy rating can be utilized in requesting feedback information and included in the feedback data to improve subsequent detections.

Image Registration: The series of detected regions of interest captured from acquired images can be projected onto a coordinate space. Projecting a series of regions of interest onto a coordinate space can assist in generating a stable view of the underlying fundus by minimizing movement and distortion inherent in a series of images.

Figure 8:
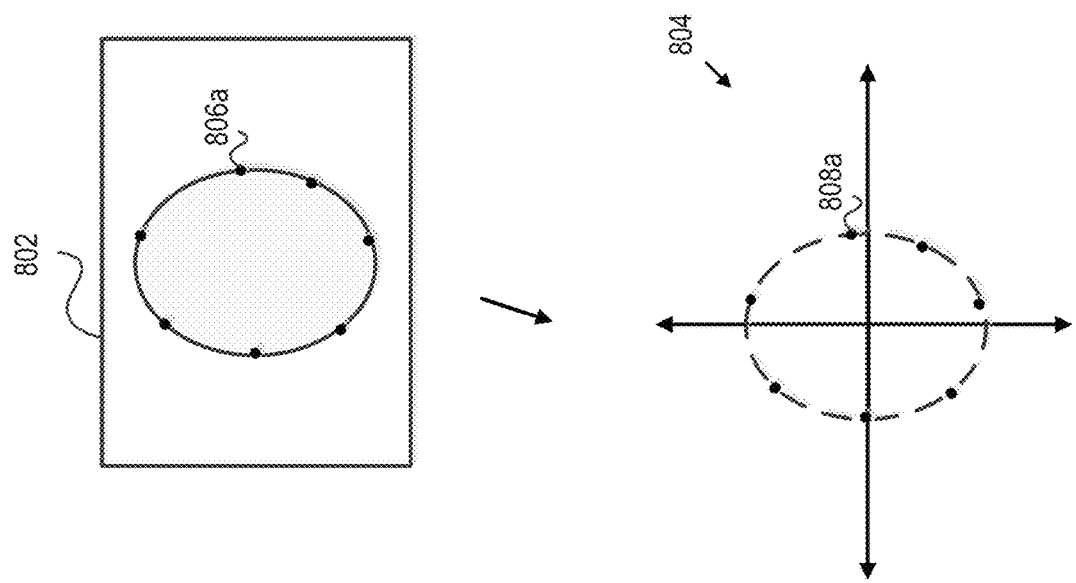
FIG. 8 is an example of projecting a detected region of interest into a corresponding coordinate space in accordance with embodiments of the present technology.

FIG. 8 is an example of projecting a detected region of interest into a corresponding coordinate space 804 in accordance with embodiments of the present technology. As shown in FIG. 8, points (e.g., 806*a*) of the detected region of interest in image 802 can be projected as points (e.g., 808*a*) on the coordinate space 804. For example, pixels (e.g., point 806*a*) included in the region of interest can transform into coordinates (e.g., point 808*a*) on the coordinate space 804.

The coordinate space 804 can include a 2-dimensional (x-axis and y-axis) or 3-dimensional (x-axis, y-axis, z-axis) region including one or more overlapping detected regions of interest. For instance, similar positions of regions of interest can overlap one another in the coordinate space, which can be utilized in generating an output image, as discussed in greater detail below.

The projection of each detected regions of interest onto coordinate space 804 may be performed using any transformation technique (affine, homology, etc.). Transforms may be calculated between regions of interest using any image alignment technique (enhanced correlation coefficient, RANSAC, etc.).

A series of transforms between regions of interest that are adjacent in time may be concatenated to produce a single transform that maps the first region of interest to the coordinate space. Transforms between spatially overlapping regions of interest that are not adjacent in time may be used to correct for errors that arise when computing transforms between regions of interest that are adjacent in time.

Figure 9:
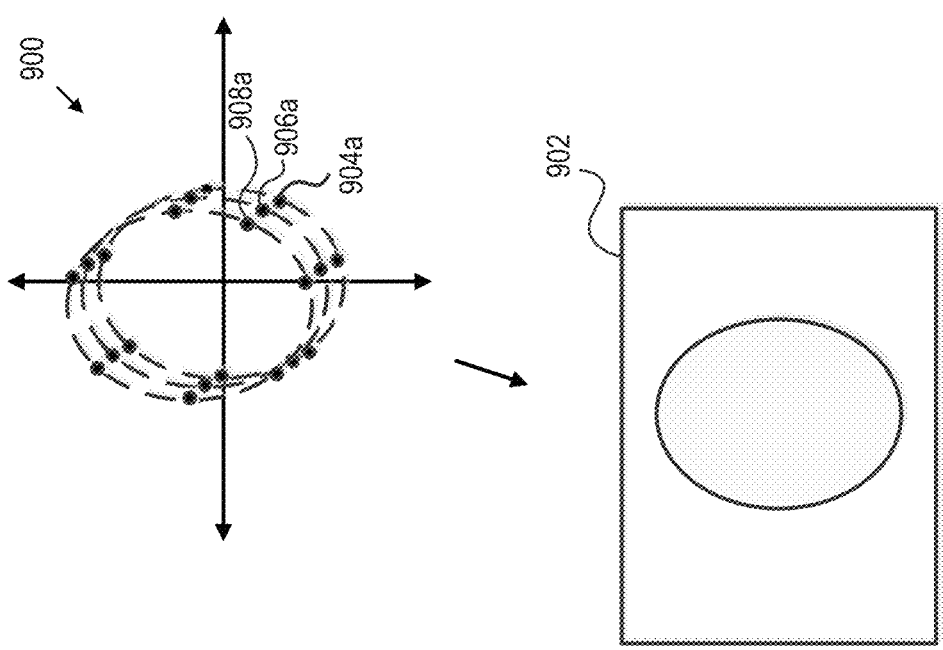
FIG. 9 is an example of generating an output image from the coordinate plane in accordance with embodiments of the present technology.

Output Image Generation: The points included in the coordinate plane may be combined to generate an output image. FIG. 9 is an example of generating an output image 902 from the coordinate plane 900 in accordance with embodiments of the present technology. As shown in FIG. 9, a series of points (e.g., points 904a, 906a, 908a) on the coordinate plane can be utilized in generating an output image representative of the fundus.

As noted above, a series of overlapping regions of interest of images can be combined in generating the output image. For example, a pixel of a region of interest of a first image is represented with point 904a, and a pixel of a region of interest of a second image is represented with point 906a. Corresponding points (e.g., points 904a, 906a) on the coordinate plane 900 can be combined in generating an output image 902.

In implementations where the original fundus image data includes a single fundus image for each point in time, overlapping regions of interest may be combined into a single, larger image by tiling the overlapping regions of interest from various points in time in adjacent rows and columns. A model processing this composite image may include a feedforward machine learning model that is configured by being trained on appropriately labeled training data to process the composite input image and to generate a model output that is an image indicative of a fundus. In some embodiments, the output may be a super-resolution image (i.e. may have a higher resolution than the input images). For example, a fundus image processing machine learning model may be a deep convolutional neural network.

Alternatively, a model for processing overlapping regions of interest may be a recurrent machine learning model that has been configured by being trained on appropriately labeled training data to process a series of overlapping regions of interest one by one to, for each image, update the internal state of the model, and to, after a certain number of images in the sequence have been processed, generate a model output that is an image indicative of a fundus. In some embodiments, the output may be a super-resolution image. For example, a fundus image processing machine learning model may be a recurrent neural network that includes one or more long short-term memory (LSTM) layers.

In implementations where the fundus image data includes multiple fundus images for each point in time where each depicts the fundus of a patient from a different perspective, various combinations of overlapping regions of interest may be combined into one or multiple, larger images by tiling the overlapping regions of interest from various perspectives and/or points in time in adjacent rows and columns. A model processing these composite images may be a feedforward fundus image processing machine learning model that has been configured by being trained on appropriately labeled training data to process the composite input images simultaneously to generate a model output that is a 3D image indicative of a fundus. In some embodiments, the output may be a super-resolution 3D image. For example, the fundus image processing machine learning model may be a deep convolutional neural network that includes multiple towers of convolutional layers.

Alternatively, a model for processing overlapping regions of interest from multiple perspectives may be a recurrent machine learning model that has been configured by being trained on appropriately labeled training data to process a series of overlapping regions of interest from multiple perspectives one by one to, for each set of images, update the internal state of the model, and to, after a certain number of image sets in the sequence have been processed, generate a model output that is a 3D image indicative of a fundus. In some embodiments, the output may be a super-resolution 3D image. For example, a fundus image processing machine learning model may be a recurrent neural network that includes one or more long short-term memory (LSTM) layers.

Figure 10:
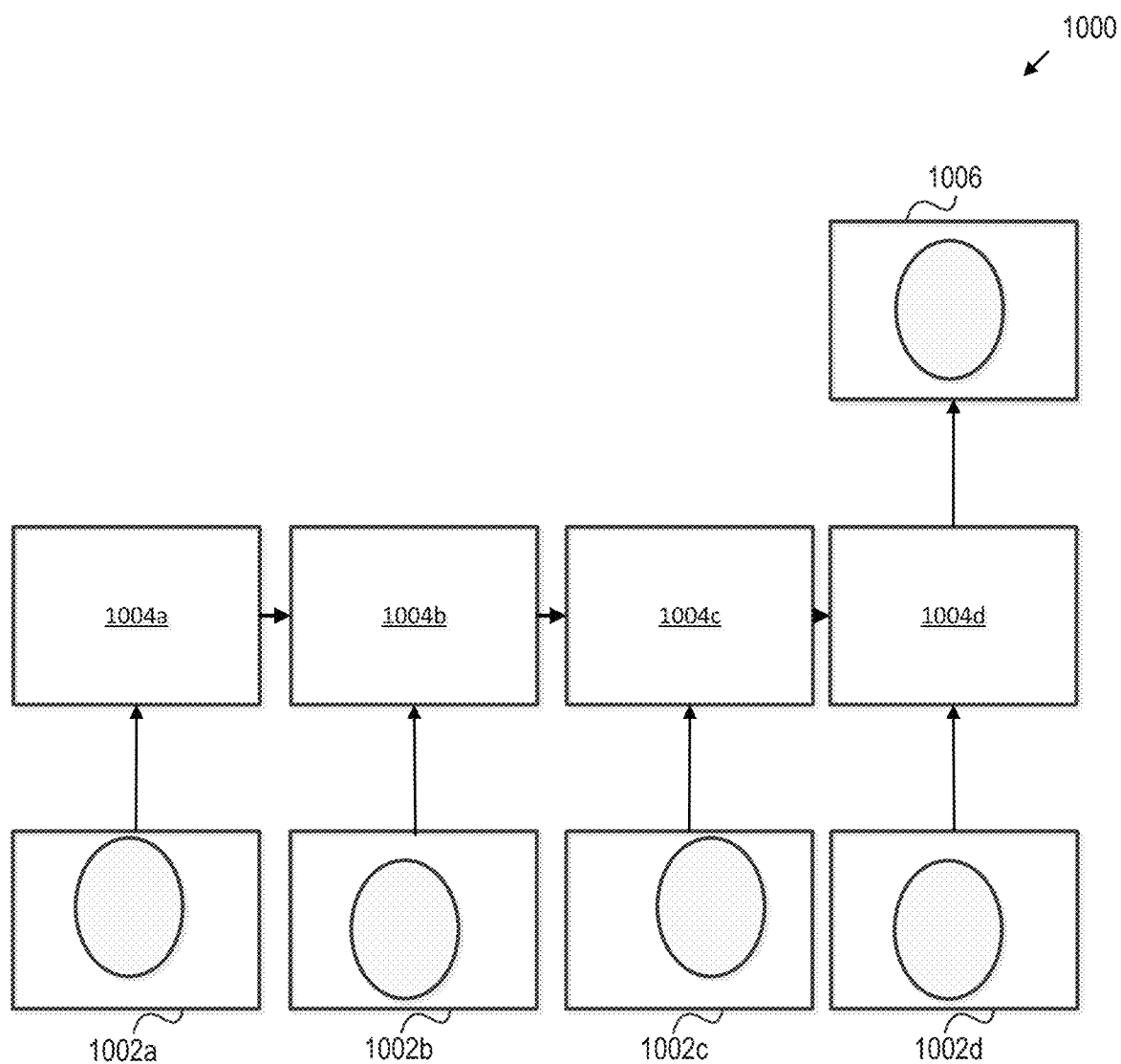
FIG. 10 is a block diagram of an example set of segmented images collapsed into an output image in accordance with embodiments of the present technology.

FIG. 10 is a block diagram 1000 of an example set of segmented images 1002a-d collapsed into an output image 1006 in accordance with embodiments of the present technology. As shown in FIG. 10, projected images 1002a-d projected onto the coordinate space can be combined into an output image 1006. For example, internal states 1004a-d can be updated for each projected image 1002a-d and used to generate the output image 1006.

In a first case, characteristics of corresponding pixels/features can be averaged. Averaging characteristics of overlapping pixels can create a resultant pixel in the output image 1006 that is based on a series of processed images. In this case, the resolution of the output image may be similar or equal to that of the resolution of the input images.

In a second case, corresponding pixels/features can be combined so as to create an output image with an increased resolution (or a "super-resolution image"). In this case, pixels depicting a similar portion of a fundus can be combined such that the resolution of that portion of the fundus is increased. Generating the super-resolution image may include identifying corresponding points on the coordinate space that represent overlapping features of the region of interest. The super-resolution image can provide an accurate depiction of the fundus that can be magnified to provide a more detailed inspection of the fundus. The stacked overlapping regions of interest on the coordinate space can be an input in a convolutional neural network which produces a super-resolution fundus photograph as an output. In some embodiments, the stacked overlapping regions of interest can be provided as inputs into a recurrent neural network which produces a super-resolution fundus photograph as the output.

In the following description, numerous specific details are set forth such as examples of specific components, circuits, and processes to provide a thorough understanding of the present disclosure. Also, in the following description and for purposes of explanation, specific nomenclature is set forth to provide a thorough understanding of the present embodiments. However, it will be apparent to one skilled in the art that these specific details may not be required to practice the present embodiments. In other instances, well-known circuits and devices are shown in block diagram form to avoid obscuring the present disclosure.

The term "coupled" as used herein means connected directly to or connected through one or more intervening components or circuits. Any of the signals provided over various buses described herein may be time-multiplexed with other signals and provided over one or more common buses. Additionally, the interconnection between circuit elements or software blocks may be shown as buses or as single signal lines. Each of the buses may alternatively be a single signal line, and each of the single signal lines may alternatively be buses, and a single line or bus might represent any one or more of a myriad of physical or logical mechanisms for communication (e.g., a network) between components. The present embodiments are not to be construed as limited to specific examples described herein but rather to include within their scope all embodiments defined by the appended claims.

Selected Embodiments of Suitable Computing Environments

Figure 11:
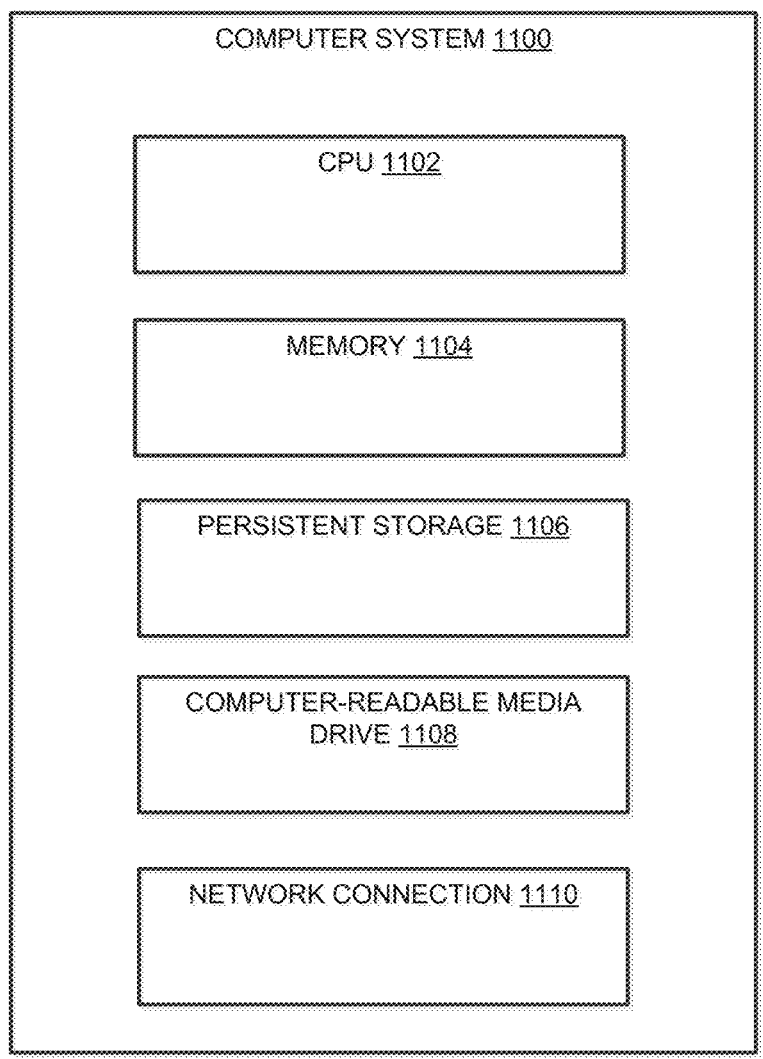
FIG. 11 is a block diagram showing components typically incorporated in at least some of the computer systems and other devices on which the present system operates in accordance with embodiments of the present technology.

FIG. 11 is a block diagram showing components typically incorporated in at least some of the computer systems and other devices on which the present system operates in accordance with embodiments of the present technology. In various embodiments, these computer systems and other devices 1100 can include server computer systems, desktop computer systems, laptop computer systems, netbooks, mobile phones, personal digital assistants, televisions, cameras, automobile computers, electronic media players, etc. In various embodiments, the computer systems and devices include zero or more of each of the following: a central processing unit ("CPU") 1101 for executing computer programs; a computer memory 1102 for storing programs and data while they are being used, an operating system including a kernel, and device drivers; a persistent storage device 1103, such as a hard drive or flash drive for persistently storing programs and data; a computer-readable media drive 1104 that are tangible storage means that do not include a transitory, propagating signal, such as a floppy, CD-ROM, or DVD drive, for reading programs and data stored on a computer-readable medium; and a network connection 1105 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the components as described herein can be implemented using devices of various types and configurations and having various components.

Figure 12:
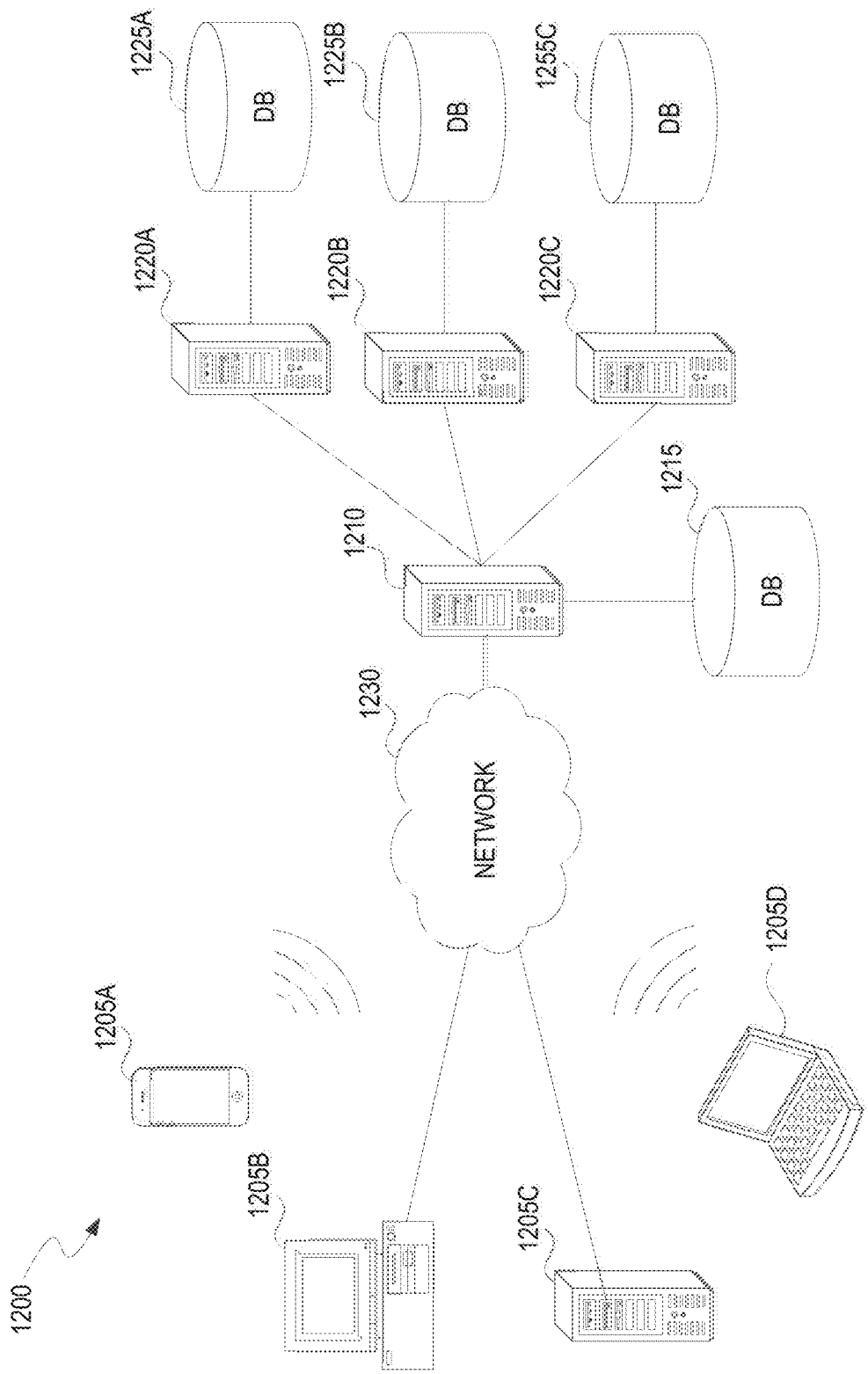
FIG. 12 is a system diagram illustrating an example of a computing environment in which the present embodiments may be implemented in accordance with embodiments of the present technology.

FIG. 12 is a system diagram illustrating an example of a computing environment in which the present embodiments may be implemented in accordance with embodiments of the present technology. In some implementations, environment 1200 includes one or more client computing devices 1205A-D. Client computing devices 1205 operate in a networked environment using logical connections 1210 through network 1230 to one or more remote computers, such as a server computing device.

In some implementations, server 1210 is an edge server which receives client requests and coordinates fulfillment of those requests through other servers, such as servers 1220A-C. In some implementations, server computing devices 1210 and 1220 comprise computing systems. Though each server computing device 1210 and 1220 is displayed logically as a single server, server computing devices can each be a distributed computing environment encompassing multiple computing devices located at the same or at geographically disparate physical locations. In some implementations, each server 1220 corresponds to a group of servers.

Client computing devices 1205 and server computing devices 1210 and 1220 can each act as a server or client to other server/client devices. In some implementations, servers (1210, 1220A-C) connect to a corresponding database (1215, 1225A-C). As discussed above, each server 1220 can correspond to a group of servers, and each of these servers can share a database or can have its own database. Databases 1215 and 1225 warehouse (e.g., store) information such as user data (e.g., user identifiers, user profiles, etc.), web page data, machine learning models, performance parameters, and so on. Though databases 1215 and 1225 are displayed logically as single units, databases 1215 and 1225 can each be a distributed computing environment encompassing multiple computing devices, can be located within their corresponding server, or can be located at the same or at geographically disparate physical locations.

Network 1230 can be a local area network (LAN) or a wide area network (WAN) but can also be other wired or wireless networks. In some implementations, network 1230 is the Internet or some other public or private network. Client computing devices 1205 are connected to network 1230 through a network interface, such as by wired or wireless communication. While the connections between server 1210 and servers 1220 are shown as separate connections, these connections can be any kind of local, wide area, wired, or wireless network, including network 1230 or a separate public or private network.

CONCLUSION

Unless contrary to physical possibility, it is envisioned that (i) the methods/steps described above may be performed in any sequence and/or in any combination, and that (ii) the components of respective embodiments may be combined in any manner.

The techniques introduced above can be implemented by programmable circuitry programmed/configured by software and/or firmware, or entirely by special-purpose circuitry, or by a combination of such forms. Such special-purpose circuitry (if any) can be in the form of, for example, one or more application-specific integrated circuits (ASICs), programmable logic devices (PLDs), field-programmable gate arrays (FPGAs), etc.

Software or firmware to implement the techniques introduced here may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible medium can include recordable/non-recordable media (e.g., read-only memory (ROM), random access memory (RAM), magnetic disk storage media, optical storage media, flash memory devices, etc.).

Any of the steps as described in any methods or flow processes herein can be performed in any order to the extent the steps in the methods or flow processes remain logical.

Note that any and all of the embodiments described above can be combined with each other, except to the extent that it may be stated otherwise above or to the extent that any such embodiments might be mutually exclusive in function and/or structure.

Although the present invention has been described with reference to specific exemplary embodiments, it will be recognized that the invention is not limited to the embodiments described but can be practiced with modification and alteration within the spirit and scope of the appended claims. Accordingly, the specification and drawings are to be regarded in an illustrative sense rather than a restrictive sense.

I claim:
1. A computer-implemented method for generating a fundus image captured by an ophthalmic imaging apparatus, the method comprising:
acquiring a stream of images from an imaging sensor disposed on an ophthalmic imaging apparatus;

for each acquired image in the stream of images, inspecting the image to determine a fundus region of the image indicative of a fundus;

for each image in the stream of images, processing each image to modify an internal state of a recurrent model by combining both each image and a previous internal state of the recurrent model;

responsive to processing a threshold number of images, generating an output that indicates a portion of each image that is indicative of the fundus utilizing the internal state of the recurrent model;

projecting each detected fundus region onto a coordinate space, wherein multiple detected fundus regions of images in the stream of images are configured to overlap one another in the coordinate space;

generating a fundus image by combining the overlapping detected fundus regions on the coordinate space; and outputting the fundus image to a device to be displayed on an interface executing on the device.

2. The computer-implemented method of claim 1, further comprising:

concatenating a series of transforms included between determined fundus regions on the coordinate space that are adjacent to one another with respect to time to generate a first transform that maps a first fundus region of a first image of the stream of images to the coordinate space.

3. The computer-implemented method of claim 1, further comprising:

processing the stream of images using a recurrent machine learning model trained using training data to update an internal state of the recurrent machine learning model based on overlapping fundus regions determined in each image of the stream of images, wherein the stream of images depicts multiple perspectives of the fundus, and wherein the outputted fundus image includes a three-dimensional image depicting the fundus that is generated based on the updated internal state of the recurrent machine learning model.

4. The computer-implemented method of claim 1, further comprising:

comparing the determined fundus region of a first image of the stream of images with an internal model to determine a number of corresponding characteristics between the determined fundus region of the first image and the internal model;

determining whether the number of corresponding characteristics falls below a threshold value; and responsive to determining that the number of corresponding characteristics falls below the threshold value, rejecting the image from being projected onto the coordinate space.

5. The computer-implemented method of claim 1 wherein generating the fundus image further comprises:

identifying positions on the coordinate space with overlapping pixels indicative of similar positions of multiple detected fundus regions on the coordinate space; and averaging pixel characteristics of the overlapping pixels included in the identified positions on the coordinate space with overlapping pixels in the fundus image.

6. The computer-implemented method of claim 1 wherein generating the fundus image further comprises:

identifying positions on the coordinate space with overlapping pixels indicative of similar positions of multiple detected fundus regions on the coordinate space; and combining the overlapping pixels included in the identified positions on the coordinate space with overlapping pixels, wherein the fundus image includes the combined overlapping pixels that provides a higher resolution than that of any image included in the stream of images.

7. The computer-implemented method of claim 1 wherein acquiring the stream of images comprises acquiring the stream of images from an indirect ophthalmoscope having at least one imaging sensor configured to capture the stream of images.

8. The computer-implemented method of claim 7, further comprising:

obtaining, by two imaging sensors included on the indirect ophthalmoscope, multiple images indicative of the fundus from varying perspectives; and combining the obtained multiple images by the two imaging sensors to generate a stereoscopic image indicative of the fundus, each stereoscopic image included as one of the images included in the stream of images.

9. The computer-implemented method of claim 8, further comprising:

capturing an initialization image by a wide-angle image sensor on the indirect ophthalmoscope;

determining whether the initialization image depicts the fundus; and responsive to determining that the initialization image depicts the fundus, capturing, by the two imaging sensors disposed adjacent to the wide-angle image sensor on the indirect ophthalmoscope, multiple images indicative of the fundus from varying perspectives.

10. A method performed by an ophthalmic imaging apparatus to generate a fundus image, the method comprising:

acquiring an image from the ophthalmic imaging apparatus;

detecting a region of interest indicative of a fundus by comparing the image with a model and modifying an internal state of the model based on features of the image;

comparing the detected region of interest of the image with the model to determine a number of corresponding characteristics between the detected region of interest of the image and the model;

determining whether the number of corresponding characteristics falls below a threshold value;

responsive to determining that the number of corresponding characteristics falls below the threshold value, rejecting the image from being projected onto the coordinate space;

projecting the detected region of interest onto a coordinate space;

concatenating a series of transforms included between detected regions of interest on the coordinate space that are adjacent to one another with respect to time to generate a final transform that maps the region of interest of the image to the coordinate space;

combining overlapping regions of interest on the coordinate space to generate a fundus image; and outputting the fundus image.

11. The method of claim 10, further comprising:

acquiring a stream of images representative of the fundus by an imaging sensor on the ophthalmic imaging device, wherein the stream of images is utilized in generating the fundus image.

12. The method of claim 10, further comprising:

for each image in a stream of images that includes the image, processing each image to modify an internal state of a recurrent model by combining both each image and a previous internal state of the recurrent model; and responsive to processing a threshold number of images, generating an output that indicates a portion of each image that is indicative of the region of interest utilizing the internal state of the recurrent model.

13. The method of claim 10, further comprising:

processing a stream of images using the model trained using training data to update an internal state of the model based on overlapping regions of interest detected in each image of the stream of images, wherein the model includes a recurrent machine learning model, wherein the stream of images depicts multiple perspectives of the fundus, and wherein the outputted fundus image includes a three-dimensional image depicting the fundus that is generated based on the updated internal state of the model.

14. The method of claim 10 wherein said generating the fundus image further comprises:

identifying positions on the coordinate space with overlapping pixels indicative of similar positions of multiple detected regions of interest on the coordinate space; and combining the overlapping pixels included in the identified positions on the coordinate space with overlapping pixels, wherein the fundus image includes the combined overlapping pixels that provides a higher resolution than that of any image included in the stream of images.

15. An ophthalmic imaging system, comprising:

an ophthalmic imaging apparatus comprising an imaging sensor configured to capture a stream of images representative of a fundus; and a processor communicatively coupled to the imaging sensor, wherein the processor is configured to— for at least a portion of the images in the stream of images, detect a fundus region indicative of the fundus by comparing each image with a recurrent model and modifying an internal state of the recurrent model based on features of the image;

project each detected fundus region onto a coordinate space, wherein multiple detected fundus regions of images in the stream of images are configured to overlap one another in the coordinate space;

identify positions on the coordinate space with overlapping pixels indicative of similar positions of multiple detected fundus regions on the coordinate space; and combine the overlapping pixels included in the identified positions on the coordinate space with overlapping pixels;

generate a fundus image by combining the overlapping detected fundus regions on the coordinate space, wherein the fundus image includes the combined overlapping pixels that provides a higher resolution than that of any image included in the stream of images; and display the fundus image on an interface executing on a user device.

16. The ophthalmic imaging system of claim 15 wherein the processor is further configured to:

for each image in the stream of images, process each image to modify an internal state of a recurrent model by combining both an input image and a previous internal state of the recurrent model; and responsive to processing a threshold number of images, generate an output that indicates a portion of each image that is indicative of the fundus utilizing the internal state of the recurrent model.

17. The ophthalmic imaging system of claim 15 wherein:

the imaging sensor comprises two stereoscopic imaging sensors configured to capture multiple images indicative of the fundus from varying perspectives, wherein the multiple images are configured to be combined to generate a stereoscopic image indicative of the fundus, each stereoscopic image included as one of the images included in the stream of images.

18. The ophthalmic imaging system of claim 15 wherein the ophthalmic imaging system further comprises an attachment mechanism configured to secure the ophthalmic imaging apparatus to a binocular indirect ophthalmoscope.

19. The ophthalmic imaging system of claim 15 wherein the ophthalmic imaging system further comprises binocular indirect ophthalmoscope, the imaging sensor being integrated into the binocular indirect ophthalmoscope.

* * * * *